US012270980B2

(12) United States Patent
Graham et al.

(10) Patent No.: US 12,270,980 B2
(45) Date of Patent: Apr. 8, 2025

(54) BINOCULAR DEVICE FOR VISUALIZING OPTICAL RADIATION AND METHOD OF VISUALIZING OPTICAL RADIATION

(71) Applicant: i-Med Technology B.V., Maastricht (NL)

(72) Inventors: Vincent Graham, Maastricht (NL); Fokko Pieter Wieringa, Elst (NL)

(73) Assignee: i-Med Technology B.V., Maastricht (NL)

( * ) Notice: Subject to any disclaimer, the term of this patent is extended or adjusted under 35 U.S.C. 154(b) by 537 days.

(21) Appl. No.: 17/635,434

(22) PCT Filed: Aug. 20, 2020

(86) PCT No.: PCT/NL2020/050522
§ 371 (c)(1),
(2) Date: Feb. 15, 2022

(87) PCT Pub. No.: WO2021/034199
PCT Pub. Date: Feb. 25, 2021

(65) Prior Publication Data
US 2022/0308328 A1 Sep. 29, 2022

(30) Foreign Application Priority Data
Aug. 22, 2019 (NL) ..................................... 2023688

(51) Int. Cl.
*G02B 21/20* (2006.01)
*A61B 90/00* (2016.01)
(Continued)

(52) U.S. Cl.
CPC ............ *G02B 21/20* (2013.01); *A61B 90/361* (2016.02); *G02B 21/0012* (2013.01);
(Continued)

(58) Field of Classification Search
CPC .......................... G02B 21/20; G02B 21/0012; G02B 27/0172; G02B 27/288; G02B 2027/0134;
(Continued)

(56) References Cited

U.S. PATENT DOCUMENTS 5,841,509 A     11/1998   Harooni et al.
2014/0327837 A1 11/2014   Osterman et al.
(Continued)

FOREIGN PATENT DOCUMENTS

EP          1566142 A1      8/2005
JP       2007114168 A  *    5/2007
(Continued)

OTHER PUBLICATIONS

Plattner Michael et al: "Filtering Specular Reflections by Merging Stereo Images", May 12, 2019, Advances in Databases and Information Systems; [Lecture Notes in Computer Science; Lect.Notes Computer], Springer International Publishing, Cham, pp. 164-172.
(Continued)

*Primary Examiner* — Arnel C Lavarias
(74) *Attorney, Agent, or Firm* — N.V. Nederlandsch Octrooibureau

(57) ABSTRACT

A binocular device for visualizing optical radiation includes a support structure, a left camera, and a right camera coupled to the support structure. The left camera includes left optics and a left image sensor, and the right camera includes right optics and a right image sensor. The left image sensor and the right image sensor are configured to create left and right video signals from detected optical radiation received from the corresponding left and right input optics about a same field of view along respective left and right input optical axes. A specular reflection is detected.

19 Claims, 13 Drawing Sheets

(51) Int. Cl.
  *G02B 21/00* (2006.01)
  *G02B 27/01* (2006.01)
  *G02B 27/28* (2006.01)
  *A61B 90/50* (2016.01)

(52) U.S. Cl.
  CPC ....... *G02B 27/0172* (2013.01); *G02B 27/288* (2013.01); *A61B 2090/502* (2016.02); *G02B 2027/0134* (2013.01)

(58) Field of Classification Search
  CPC ...... G02B 7/00; G02B 21/00; G02B 21/0004; G02B 21/06; G02B 21/18; G02B 21/36; G02B 21/367; G02B 21/368; G02B 23/00; G02B 23/16; G02B 23/18; G02B 27/0025; G02B 27/01; G02B 27/0101; G02B 2027/0118; G02B 2027/012; G02B 2027/0121; G02B 2027/0132; G02B 2027/0138; G02B 27/017; A61B 90/361; A61B 2090/502
  USPC ....... 359/375, 362, 363, 368, 369, 385, 407, 359/419, 350, 355, 480, 482, 601, 609, 359/613, 614
  See application file for complete search history.

(56) References Cited

U.S. PATENT DOCUMENTS

2017/0143442 A1   5/2017   Tesar et al.
2018/0303574 A1   10/2018  Ramirez Luna et al.

FOREIGN PATENT DOCUMENTS

JP   2017-148657 A   8/2017
JP   2018-063378 A   4/2018
WO   2018/105411 A1  6/2018

OTHER PUBLICATIONS

Khor et al: "Augmented and virtual reality in surgery—the digital surgical environment: applications, limitations and legal pitfalls"; Jul. 30, 2016.

Nishimoto et al: "An augmented reality system in lymphaticovenous anastomosis surgery", Journal of Surgical Case Reports, 2016; 5, 1-3.

Vávra et al: "Recent Development of Augmented Reality in Surgery: A Review", Journal of Healthcare Engineering vol. 2017, Article ID 4574172, 1-9.

Wieringa et al: "Contrast enhancement of coronary arteries in cardiac surgery: a new multispectral stereoscopic camera technique", 2019.

Ai et al: "Augmented reality based real-time subcutaneous vein imaging system", Biomedical Optics Express 2565, Jul. 1, 2016, vol. 7, No. 7.

Mitchell et al: "AR and Lymphaticovenous Anastomosis Surgery", Jun. 26, 2017.

* cited by examiner

BINOCULAR DEVICE FOR VISUALIZING OPTICAL RADIATION AND METHOD OF VISUALIZING OPTICAL RADIATION

FIELD OF THE INVENTION

The invention relates to a binocular device for visualizing optical radiation. The invention further relates to a binocular device for visualizing visible and invisible radiation.

BACKGROUND OF THE INVENTION

When performing a surgical procedure, the surgeon uses bright lights in the operation room in order to be able to distinguish the tissues to be treated as good as possible. However, not everything can be seen clearly in that way. For example, certain tissue types, such as certain tumors, are not visible by the human eye. Those tissue types can sometimes be visualized by a technique of near-infrared imaging. This may be the case for tumor tissue.

"Binocular Goggle Augmented Imaging and Navigation System provides real-time fluorescence image guidance for tumor resection and sentinel lymph node mapping", by Suman B. Mondal et al., in Scientific Reports, vol. 5, no. 1, July 2015, discloses a system comprising a near-infrared (NIR) source comprising LEDs and bandpass filters and white flashlights or surgical light covered with short-pass filters as the white light source. An imaging module collects combined color-NIR signal via a custom glass lens. The incoming signal was divided into visible and NIR components by a custom dichroic beam-splitter cube and directed to a separate color and NIR sensor. The NIR and color sensors were co-registered. A personal computer with an operating system, such as a Windows® x64 PC, generates superimposed color-NIR images, creates a GUI that gives access to display, store, and processing functions of image data and duplicates images for display on the PC and a head-mounted display module simultaneously. The display module consists of a head-mounted display.

SUMMARY OF THE INVENTION

It would be advantageous to provide an improved visualization device. To address this concern, according to an aspect of the invention, a binocular device is provided for visualizing optical radiation, comprising
  a support structure;
  a left camera and a right camera coupled to the support structure, the left camera comprising left optics and a left image sensor, the right camera comprising right optics and a right image sensor, the left image sensor and the right image sensor being configured to create left and right video signals from detected optical radiation received from the corresponding left and right input optics about a same field of view along respective left and right input optical axes;
  the device further comprising a processing unit configured to:
  receive a signal representing a left image from the left camera and a right image from the right camera, the left image and the right image being captured substantially simultaneously by the left camera and the right camera, respectively;
  compare the left image to the right image; and
  detect a specular reflection based on a result of the comparison.

According to another aspect, a method of visualizing optic radiation is provided, the method comprising
  receiving radiation, about a same field of view along respective left and right input optical axes, by left and a right input optics coupled to a support structure, and transmitting the light onto a left image sensor of a left camera and a right image sensor of a right camera, respectively, the left camera and the right camera being coupled to the support structure; and
  creating left and right video signals from the detected radiation received by the left camera and the right camera, respectively;
  receiving, by a processor, a signal representing a left image from the left camera and a right image from the right camera, the left image and the right image being captured substantially simultaneously by the left camera and the right camera, respectively;
  comparing, by the processor, the left image to the right image; and
  detecting, by the processor, a specular reflection based on a result of the comparison.

According to another aspect, a binocular device is provided for visualizing optical radiation, the device comprising
  a support structure;
  a left camera and a right camera coupled to the support structure, the left camera comprising left optics and a left image sensor, the right camera comprising right optics and a right image sensor, the left image sensor and the right image sensor being configured to create left and right video signals from detected optical radiation received from the corresponding left and right input optics about a same field of view along respective left and right input optical axes;
  a left display and a right display coupled to the support structure and arranged to be viewed by a pair of eyes of a user through a left eyepiece operatively connected to the left display and a right eyepiece operatively connected to the right display, wherein the left display and the right display are configured to present left and right video images, formed with visible light by the left display and the right display, based respectively on the left and right video signals;
  wherein the binocular device is configured to, in a particular visualization mode, alternatingly show a left image based on the left video signals on the left display and a right image based on the right video signals on the right display.

This allows a user to distinguish a specular reflection.

According to another aspect, a method of visualizing optic radiation is provided, the method comprising
  receiving radiation, about a same field of view along respective left and right input optical axes, by left and a right input optics coupled to a support structure, and transmitting the light onto a left image sensor of a left camera and a right image sensor of a right camera, respectively, the left camera and the right camera being coupled to the support structure; and
  creating left and right video signals from the detected radiation received by the left camera and the right camera, respectively;
  presenting, by a left display and a right display coupled to the support structure and to be viewed by a pair of eyes of a user through a left eyepiece operatively connected to the left display and a right eyepiece operatively connected to the right display, left and right video images formed with visible light based respectively on the left and right video signals, wherein the presenting comprises, in a particular visualization mode, alternatingly showing a left image based on the left video signals on the left display and a right image based on the right video signals on the right display.

This allows a user to distinguish a specular reflection.

It would be advantageous to provide an improved visualization device. To address this concern, according to an aspect of the invention, a binocular device is provided for visualizing visible and invisible radiation. The binocular device comprises a support structure;

a left camera and a right camera coupled to the support structure, the left camera comprising left optics and a left image sensor, the right camera comprising right optics and a right image sensor;

the left image sensor and the right image sensor being configured to create left and right video signals from detected optical radiation received from the corresponding left and right input optics about a same field of view along respective left and right input optical axes, at least one of the cameras being sensitive to both radiation in an invisible wavelength band of radiation and radiation in a visible light wavelength band of radiation, the input optics of said at least one of the cameras being transmissive for the invisible wavelength band and reductive for the visible light wavelength band.

The combination of features may help to present a stereoscopically realistic depiction of features in the visible light wavelength range and the invisible wavelength range. The input optics that is transmissive for the invisible wavelength band and reductive for the visible light wavelength band may help to improve image quality. This is based on the notion that the intensity of received invisible radiation, such as infrared radiation, is in most cases much less than the intensity of visible light. In many practical situations, the visible light is abundantly present, while the intensity of the invisible wavelength band of radiation is much less. The reduction of the visible light wavelength band of radiation, without reducing the invisible wavelength band of radiation too much, brings the intensity levels of both wavelength bands of radiation closer together. This may improve image quality, in particular in combination with low-cost and/or light-weight optics and image sensors.

For example, the infrared may be near-infrared (NIR). In applications of viewing diffuse-reflecting or fluoroscopic radiation in the near-infrared wavelength band of radiation, the intensity of the received relevant near-infrared radiation will in many cases be much less than the received radiation in the visible wavelength band.

The binocular device may further comprise a left display and a right display coupled to the support structure and arranged to be viewed by a pair of eyes of a user through a left eyepiece operatively connected to the left display and a right eyepiece operatively connected to the right display, wherein the left display and the right display are configured to present left and right video images, formed with visible light by the left display and the right display, based respectively on the left and right video signals. This allows to create a display device with built-in cameras and displays that provide improved visualization of radiation in the invisible wavelength band, for example in a head-mounted device or a hand-held device.

The input optics of the camera that is sensitive to radiation in the invisible wavelength band may comprise a polarizing filter comprising at least one layer of a polarizing material. A polarizing filter having the desired properties may be made up of particularly light-weight and cost-effective material. For example, the material used in many sunglasses reduces the intensity of visible light considerably while being largely transmissive to certain invisible wavelength bands of radiation, such as near-infrared and infrared.

The polarizing filter may comprise at least two layers of the polarizing material, having a mutually orthogonal polarization direction. This way, about 98% to 99% of the visible light may be blocked, in a relatively spectrally linear fashion. Moreover, about 90% to 95% of certain invisible wavelengths of radiation, such as a near-infrared wavelength range, may be transmitted through the polarizing filter.

The binocular device may further comprise a light source coupled to the support structure, capable of generating radiation within at least the invisible wavelength band and the visible light wavelength band.

Preferably, the light source is configured to generate beams of emitted visible light and invisible radiation that are aligned, for example by means of optical elements, to be substantially identical in geometrical shape and position. This way, the detected image may be more consistent.

The light source may comprise a polarizing filter configured to polarize the visible light within the visible light wavelength band output by the light source and transmit the radiation in the invisible wavelength band, wherein a polarization direction of the polarizing filter of the light source is substantially orthogonal to a polarization direction of the polarizing filter of the input optics. This is another way to reduce the amount of visible light significantly while keeping most of the invisible radiation.

The input optics corresponding to the camera that is sensitive to invisible radiation may comprise a diaphragm having an aperture, the diaphragm around the aperture being reductive for light in the visible light wavelength band, while the diaphragm is transmissive for the light in the infrared wavelength band. This allows to apply a diaphragm selectively to the visible light wavelength band while allowing the radiation in the invisible wavelength band to pass, substantially without being affected by the diaphragm. In addition to reducing the intensity of the visible light compared to the intensity of the invisible radiation, this feature allows to make improved use of the optics. Conventional lenses are known to have different focal spots for different wavelengths of radiation, due to dispersion. To enable optimal focus for each wavelength band of radiation (e.g., red, green, blue, and infrared), complex optics is necessary, for example by separating each wavelength band in a separate bundle and separately focusing each bundle using separate optics. Using a diaphragm with a relatively small aperture, the depth of focus is increased, which reduces this problem but also reduces the intensity of the radiation. Considering that the intensity of the visible light is much higher than the intensity of the radiation in the invisible wavelength band, the diaphragm as set forth herein has the advantages of a diaphragm for the visible light without reducing the low-intensity radiation in the invisible wavelength band. The depth of focus is increased for the visible light wavelength band of radiation, providing a sharp image of the visible light. This allows to optimize the focus of the input optics for the invisible wavelength band of radiation. Thereby, the input optics can be simplified because the input optics do not have to take into account the dispersion.

The input optics may comprise a lens with autofocus, wherein the autofocus is configured to bring into focus the radiation in the invisible wavelength band. This can be done by using a known autofocus functionality. This way, each wavelength band that is recorded by the camera may be made into a sharp image.

The input optics of the infrared sensitive camera may comprise an additional filter that is reductive for the light in the visible light wavelength band in addition to the diaphragm. To further reduce the visible light intensity, an additional filter for the visible light may be added, wherein the additional filter does not have an aperture.

The input optics of the camera that is sensitive to radiation of the invisible wavelength band may comprise a filter comprising iodine for selectively reducing the radiation in the visible light wavelength band. Iodine is known to reduce such radiation, while being transmissive for certain invisible wavelength bands, such as an infrared or near-infrared wavelength band.

The binocular device may comprise a processing unit configured to receive a signal representing a left image from the left camera and a right image from the right camera, the left image and the right image being captured substantially simultaneously by the left camera and the right camera, respectively, compare the left image to the right image, and detect a specular reflection based on a result of the comparison. This is convenient for detecting specular reflections. It is observed that the processing unit does not have to be fixed to the support structure. However, the processing unit may have a communication connection (wired or wireless) for exchange of the video signals with the image sensors and displays. The left image and the right image may be captured substantially simultaneously while the light source connected to the support structure is switched on to emit the visible light and the radiation in the invisible wavelength band. This way, the reflections may have a more predictable appearance.

The binocular device may further comprise a light source coupled to the support structure, for generating at least infrared light and visible light, wherein the light source is configured to intermittently emit the infrared light while keeping the visible light intensity substantially constant, wherein the camera is configured to capture at least one image with the emitted infrared light and at least one image without the emitted infrared light. This provides improved quality images, because the visual light images do not suffer from possible deterioration caused by the emitted radiation in the invisible wavelength range. Moreover, no flicker in the visible wavelength range may be caused. Moreover, this may allow to generate improved quality images by combining the image captured with the emitted infrared light with the image captured without the emitted infrared light.

The processing unit may be configured to calculate an enhanced infrared image based on the captured image with the emitted infrared light and the captured image without the emitted infrared light.

Each of the left camera and the right camera may be sensitive to radiation in the invisible wavelength band and radiation in the visible light wavelength band, while each of the left input optics and the right input optics may be transmissive for the infrared wavelength band and reductive for the visible light wavelength band. This way, the radiation in the invisible wavelength band may be made visible stereoscopically.

The image sensor of the camera that is sensitive to the radiation in the invisible wavelength band may comprise a sensor die that is sensitive to both the infrared wavelength band of radiation and the visible wavelength band of radiation, wherein the sensor die may be configured to output the video signal corresponding to both the radiation in the infrared wavelength band and the radiation in the visible wavelength band. This allows a relatively simple and lightweight design of the binocular device. Moreover, in combination with the reduction of the visible light the image quality can still be high.

According to another aspect of the invention, a method of visualizing visible and invisible radiation is provided. The method comprises receiving radiation, about a same field of view along respective left and right input optical axes, by left and a right input optics coupled to a support structure, and transmitting the light onto a left image sensor of a left camera and a right image sensor of a right camera, respectively, the left camera and the right camera being coupled to the support structure, wherein at least one of the cameras is sensitive to both radiation in an invisible wavelength band of radiation and radiation in a visible light wavelength band of radiation, wherein the input optics of the camera that is sensitive to the invisible wavelength band of radiation is transmissive for the invisible wavelength band of radiation and reductive for the visible light wavelength band of radiation;

creating left and right video signals from the detected radiation received by the left camera and the right camera, respectively;

presenting, by a left display and a right display coupled to the support structure and to be viewed by a pair of eyes of a user through a left eyepiece operatively connected to the left display and a right eyepiece operatively connected to the right display, left and right video images formed with visible light, based respectively on the left and right video signals.

The person skilled in the art will understand that the features described above may be combined in any way deemed useful. Moreover, modifications and variations described in respect of the system may likewise be applied to the method and to the computer program product, and modifications and variations described in respect of the method may likewise be applied to the system and to the computer program product.

BRIEF DESCRIPTION OF THE DRAWINGS

In the following, aspects of the invention will be elucidated by means of examples, with reference to the drawings. The drawings are diagrammatic and may not be drawn to scale. Throughout the drawings, similar items may be indicated with the same reference numerals.

DETAILED DESCRIPTION OF EMBODIMENTS

Certain exemplary embodiments will be described in greater detail, with reference to the accompanying drawings.

The matters disclosed in the description, such as detailed construction and elements, are provided to assist in a comprehensive understanding of the exemplary embodiments. Accordingly, it is apparent that the exemplary embodiments can be carried out without those specifically defined matters. Also, well-known operations or structures are not described in detail, since they would obscure the description with unnecessary detail.

Figure 1:
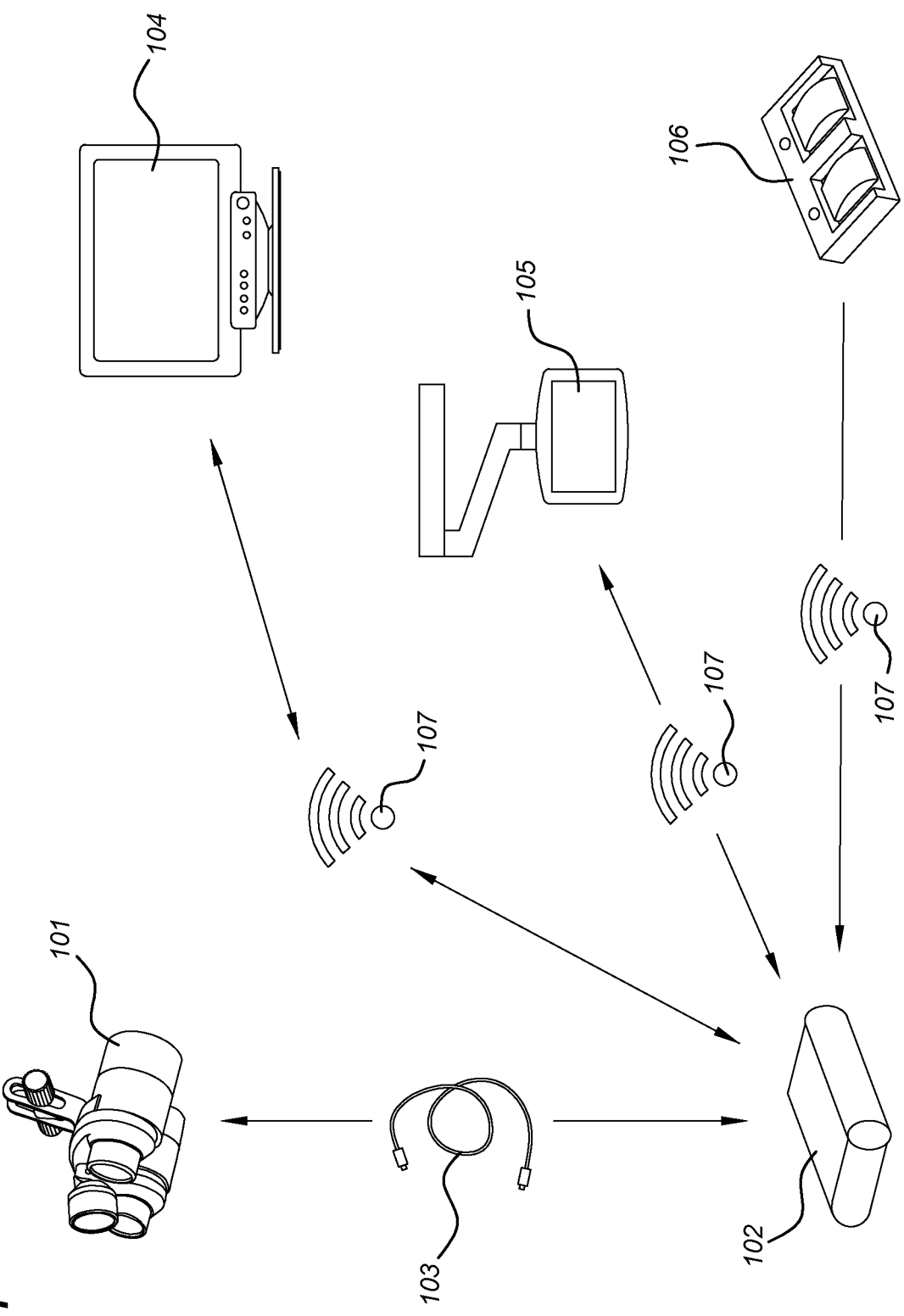
FIG. 1 shows a diagram of a system for combining visual and infrared imaging.

FIG. 1 shows an overview of an embodiment of a system for combining visual and infrared imaging. Although the system is explained here in the context of infrared imaging, a similar arrangement may be made for near-infrared or ultraviolet, or any other invisible wavelength band of radiation. The system comprises a head-mounted display 101 with a pair of built-in cameras. For example, the system is capable of magnification of the viewed pictures using for example a scale factor between 1 and 5. Recording can continue based on the original images while the user views magnified images. Full HD view with a wide-angle of 40 degrees horizontal may be provided. The system may be implemented to be wearable and autonomous. For example, the head-mounted display 101 with cameras may be provided with additional computational power by means of a wearable PC that may be carried by the user and that may be connected to the head-mounted display 101 by means of a wired (or a wireless) interface. The wearable PC and the head-mounted display 101 with cameras may be battery powered and communicate with external devices through a wireless (or a wired) connection 107. This provides the user with freedom of movement. The head mounted display 101 may have a low weight of e.g. less than 250 grams. The system may allow for 3d recording, for example through direct image streaming and recording, and may allow direct viewing of the image stream by the operating team on a larger display screen 105. The system may further comprise an external user interface device 104 that can be operated by the assistant parallel to the user of the head-mountable device 101. The user interface device 104 may be connected wired or wirelessly to the wearable PC 102 and/or directly to the head-mounted display 101. The system may further comprise a remote control by means of a foot pedal 106 or tablet, which may be connected wired or wirelessly to the wearable PC 102 and/or directly to the head-mounted display 101. The system may further be configured to provide augmented reality picture in picture overlay of pre-operative images on demand.

For example, the point of view follows the head movements of the surgeon.

Existing systems are bulky, heavy, not head-wearable, not well aligned with the eye, delayed in visualization of the processed image and not autonomous as well as having a fixed focus distance of >2 meters.

Most surgical disciplines (open or laparoscopic) such as general surgery, oncology plastic surgery, urology, gynecology, otorhinolaryngology, thorax surgery, and neurosurgery have one thing in common: the necessity to correctly identify and prevent damage to vital anatomical structures that need to be preserved (e.g. nerves, lymphatic tissue and blood vessels) and to identify the targeted tissue that needs to be removed or treated. This is challenging, especially when considering natural anatomical variations between individuals (the exact position of vital structures varies per individual). Damaging vital structures can cause severe surgical complications, such as vascular injury, ureter lesion, bile duct injury and nerve damage. Such complications have huge impact on patients and the healthcare system. Therefore, a solution that can reduce these risks is of great importance for surgeons, their patients and society as a whole.

Recognition of critical non visible anatomical structures (tissues) at working distance is desirable and may be provided by the techniques disclosed herein.

Real-time visualization (or e.g. visualization latency max 30 ms) may be provided in a head mounted 3D display 101, to be able to perform surgery with optimal spatial perception of depth and bodily orientation for extremely refined microscopic work. Longer delays in visualization are known to cause disorientation and nausea (motion sickness) when the head is freely moving, in case visual input does not match with bodily proprioception input.

Contactless recognition of critical non-visible anatomical structures (tissues) throughout normal working visual distance range (e.g. 30-50 cm) may be provided. Real-time, or very low-latency, (max 30 ms) simultaneous visual (VIS) and near-infrared (NIR) images in 3D, for augmented reality visualization with optimal spatial depth perception, may be produced. Computer analytics embedded algorithms (for example, implemented on FPGA) within the wearable computer system 102 or within the head mountable device 101 may allow to recognize (in real-time) spectral fingerprints (characteristics) of different tissue types and human organs, whilst producing an enhanced AR overlay of the critical tissues from data invisible to the human eye on the actual clinical field of view (FOV) by pixel alignment of two data streams. For example, visible light-based video stream and a video stream corresponding to a non-visible wavelength range, such as near-infrared streams for each eye to visualize in one 3D HD video stream. The system may be built around a compact lightweight (e.g. less than 250 grams), head mountable device 101 for optimal ergonomics and long term usage (up to e.g. 4-6 hours) without neck strain or eye fatigue. The system may further comprise an autonomous compact wearable computer system 102 (for example, battery powered with wireless 107 high-speed data and video transport to an external server), for optimal freedom of movement and minimum lag.

The system may be able to discern between shiny light spots caused by reflectance on the tissue versus light emission that truly originates from the tissue, by comparing the simultaneously acquired Left and Right images. The position of reflected shiny spots may differ between the Left and Right image, because of the difference in reflection angle towards the light source. The position of a light spot that is emitted by the tissue itself (e.g. due to fluorescence) or that originates from bodily contrast may however remain on the same position in a converged image. In particular where a weak signal is visualized from an added fluorescent marker or (even weaker) from bodily autofluorescence, the selective suppression of shiny spots from tissue reflection may be advantageous. This suppression method for shiny reflectance spots can be combined with other methods, such as crossed polarization between light source and camera input.

By locally processing within an FPGA, data transfer speed limitations due to longer distances may be avoided. The head-mountable device 101 may allow real-time recognition of critical non-visible tissues based on computer analytics embedded unique algorithms (FPGA) to recognize spectral signatures in real-time.

Dedicated image processing embedded software (e.g. implemented on FPGA) may cater for various display technologies (e.g. OLED, FLCoS & AMLCD) to be displayed on a single hardware platform and convert industry standard video signals to the necessary video format and control signal for the micro display. 3D Augmented Reality contrast overlay of critical tissues may be provided on the RGB visible video stream, to be able to perform surgery with optimal spatial depth perception. Dedicated software may make this possible. A head mountable autonomous system with ergonomic advantages and freedom of movement may be provided, preferably without wires connecting it to an external source.

The Head-mountable device 101 may be tethered 103 to a wearable computer 102. This may facilitate 3D recording of procedure for patient files and educational purposes, 2D play-back with real-time algorithm calculation for convergence compensation, 2D or 3D real-time (wireless 107) streaming to nearby screens 104, 105 for improved optimal teamwork, but also for remote assistance, medical patient data recording and/or educational purposes, intelligent zoom function smoothly between 1 to 5-10-20 times for optimal 3D accuracy, software adjustable 3D convergence based on working distance, cameras angle positioning from 0 to 20 degrees downwards, for optimal ergonomics (minimize neck hernia) and so that the image may be captured at the macula on the retina of the eye for optimal sharpness. The system may be used in carrying out research regarding multiple new medical application areas for tissue structure recognition (oncology, dermatology, etc.). The system can be applied to other non-medical application areas like Forensic research. Videos or information to the user (remote support) can be made to pop-up into the view of the user when needed (e.g. voice controlled, gesture or via foot pedal). The Optical brightness can automatically adapt to environmental lighting conditions for ideal viewing conditions, providing ambient through the lens light Sensing technique. Embedded IMU may register head movement of the user in 3 axes (e.g. Yaw, Pitch & Roll) in real-time in a virtual (computer generated) environment. This may allow for panoramic 3D-stitching of multiple stereoscopic images from multiple perspectives. A wireless 107 footswitch 106 and/or voice/gesture control of various functions may be provided.

The device may operate separately controllable sources for the visible (VIS) or UV, or near-infrared (NIR) spectral ranges. Both bundles may be carefully aligned. Automatic compensation for traces of near-infrared (NIR) light present within the ambient light (e.g. as with fluorescent tubes) by modulation of the NIR-lighting to obtain consecutive NIR images with NIR source on and off, thus allowing for dark-field compensation. All this without a need to modulate the visual light source (which might cause nuisance flicker, or even possibly trigger epileptic seizures).

Illumination of the anatomic structures may be performed in at least two spectral ranges: Namely the visible light and the invisible UV or near-infrared region. Lighting may be done under well-defined light conditions on light Temperature (K), Color Rendering Index (CRI), angle and beam shape. However, the system may be configured to automatically adapt to differing light conditions.

Two multi-spectral cameras (each combining the visual range by RGB video with separate UV or near-infrared spectral visualization), may be provided. A wearable computer 102 with data processing, embedded algorithms (FPGA) to recognize (real-time) spectral fingerprints of different tissue types and human organs may be provided. The user may be able to choose between various tissue types for visual augmentation. Optimal depth perception may be supported by 3D software real-time correction of parallax and convergence. Optimized data transport technology (via USB 3.2 Gen 2×2) for fast data exchange up to 40 GB/s data rate may be provided. A single cable may be implemented to control two NIR cameras and two micro-displays. Data processing of the stream of image pairs may be done externally via a tethered 103 or wirelessly connected processor in wearable computer 102 that may feed the output image to the Head Mounted Display 101 within, for example, less than 30 milliseconds. Enhanced AR overlay of critical tissue contrasts that otherwise would be invisible to the human eye may be displayed on the actual clinical field of view (FOV) by pixel alignment of two data streams to view in one 3D image. The system may cater for various display technologies (OLED, FLCoS & AMLCD) and convert industry standard video signals to the necessary data and control signal for the micro display. The system may be controlled, for example, by foot pedal, voice control or remote tablet touch screen.

Figure 2A:
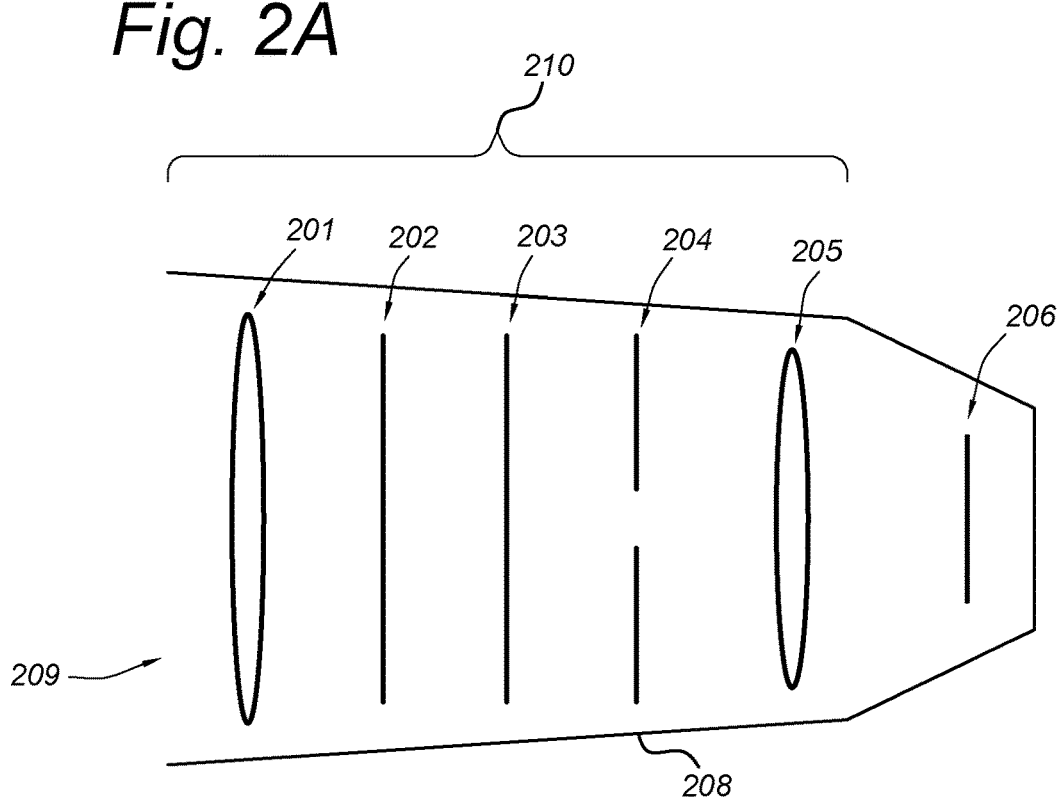
FIG. 2A shows a schematic view of a camera of a head-mounted device.

FIG. 2A shows a schematic view of a camera of a head-mounted device 101. Two cameras may be implemented, one for each eye, to support stereo viewing. The camera may comprise a housing with a wall 208 that optically isolates the optic components from outside radiation, except for the opening 209. The camera may comprise input optics 210 and an image sensor 206. The input optics 210 may comprise, from the opening 209 arranged in sequence towards the image sensor 206, a first lens 201, a notch filter 202, a visible light reduction filter 203, a visible light diaphragm 204, and a second lens 205. The order of these components may vary for different implementations, and the number and configuration of the lenses 201, 205 may be different. One or more of the lenses 201, 205 may be movable for purpose of focusing the image that is sensed by the image sensor 206. The image sensor 206 may comprise a silicon implemented sensor with coatings to make the image sensor 206 sensitive to both at least one wavelength of visible radiation, such as a red wavelength range, a green wavelength range, and a blue wavelength range, and at least one wavelength range of non-visible radiation, such as a near-infrared wavelength range, an infrared wavelength range, and/or an ultraviolet wavelength range. The optional notch filter 202 may at least partially suppress excitation of a certain undesired wavelength range.

The visible light reduction filter 203 may be adapted to suppress, or reduce, a large portion of visible light wavelengths. Moreover, the visible light reduction filter 203 may be adapted to allow to pass, or be transmissive for, light of a non-visible wavelength range, for which non-visible wavelength range the image sensor 206 is sensitive. For example, the visible light reduction filter 203 may be made of a dichroic material, which reflects or absorbs most of the light in the visible light wavelength range while transmitting most of the light in the relevant non-visible wavelength range. The visible light reduction filter 203 is adapted to allow to pass a portion of the visible light.

Examples of a suitable material for visible light reduction filter 203 and/or visible light diaphragm 204 include H-sheet Polaroid, which is a polyvinyl alcohol (PVA) polymer impregnated with iodine, and K-sheet Polaroid, which comprises aligned polyvinylidene chains in a PVA polymer created by dehydrating PVA. Another example material is a coatable polymer polarizer formed with a composition that includes a rigid rod-like polymer capable of forming a liquid crystal phase in a solvent, wherein the rigid rod-like polymer may form an achromatic polarizer, as disclosed in US 2016/0266292 A1. Yet another example material is a polarizing plate including a stretched laminate that is a laminate including a base material layer and a hydrophilic polymer layer and has undergone a stretching process, and at least a dichroic substance is adsorbed to the hydrophilic polymer layer, as disclosed in U.S. Pat. No. 8,559,105 B2. Another example is based on material usually used in dielectric beam splitters. Since it is possible to specify the wavelength at which the radiation is split, it is possible to manufacture a dielectric coating that is transparent for an invisible wavelength band of radiation, such as NIR light, and reflective for a visible light wavelength band of radiation. In this regard, it may be useful to fix the visible light filter 203 or visible light diaphragm 204 made up of a dielectric beam splitter at an angle (of e.g. 45 degrees) with respect to the optical axis of the camera (not illustrated).

The visible light diaphragm 204 is a diaphragm, which may have a fixed aperture or a variable aperture. The diaphragm is made of a material that reduces (or even completely blocks) the light in the visible light wavelength range, while being transmissive for the relevant non-visible wavelength range, such as near-infrared radiation. For example, the visible light diaphragm 204 may be made of a dichroic material that reflects or absorbs most of the light in the visible light wavelength range while transmitting most of the light in the relevant non-visible wavelength range. For example, the visible light diaphragm may be made of the same material as the visible light reduction filter 203, or a different material. The visible light diaphragm 204 may be fully non-transmissive for the light in the visible light wavelength range (except for the light passing through its aperture). Alternatively, the material of the visible light diaphragm 203 may allow to pass a (relatively small) portion of the visible light.

The lens 205 cooperates with the lens 201 to create a bundle of incoming light from the opening 209 onto the image sensor 206. The two lenses may be movable with respect to each other, in order to provide a focus function. The lenses may be transmissive for both visible light and the relevant non-visible wavelength range.

It will be noted that, although FIG. 2A shows both the visible light reduction filter 203 and the visible light diaphragm 204, this is not a limitation. In certain embodiments, either one of these components may be provided. In both cases the input optics 210 is transmissive for the relevant non-visible wavelength band and reductive for a visible light wavelength band. As stated above, the input optics does not fully block the visible light, but merely reduces it to a level that is suitable for the image sensor 206. Moreover, the input optics do not have to allow 100% of the light in the relevant invisible wavelength range to pass. Due to, for example, restrictions in available materials, the input optics does reduce the light in the relevant invisible wavelength range a bit, too.

The input optics 210 is reductive for radiation in the visible light wavelength band. For example, the intensity of radiation in the visible light wavelength band may be reduced by at least 75%, preferably by at least 90%, more preferably by at least 95%, even more preferably by at least 98%. The input optics is transmissive for radiation in the chosen invisible wavelength band. For example, the input optics may transmit at least 80% of the intensity of received radiation in the invisible wavelength band of radiation, preferably at least 90%, more preferably at least 95%. For example, reduction of visible light is at least 75% and transmission of invisible radiation is at least 80%. For example, reduction of visible light is at least 95% and transmission of invisible radiation is at least 90%.

Figure 2B:
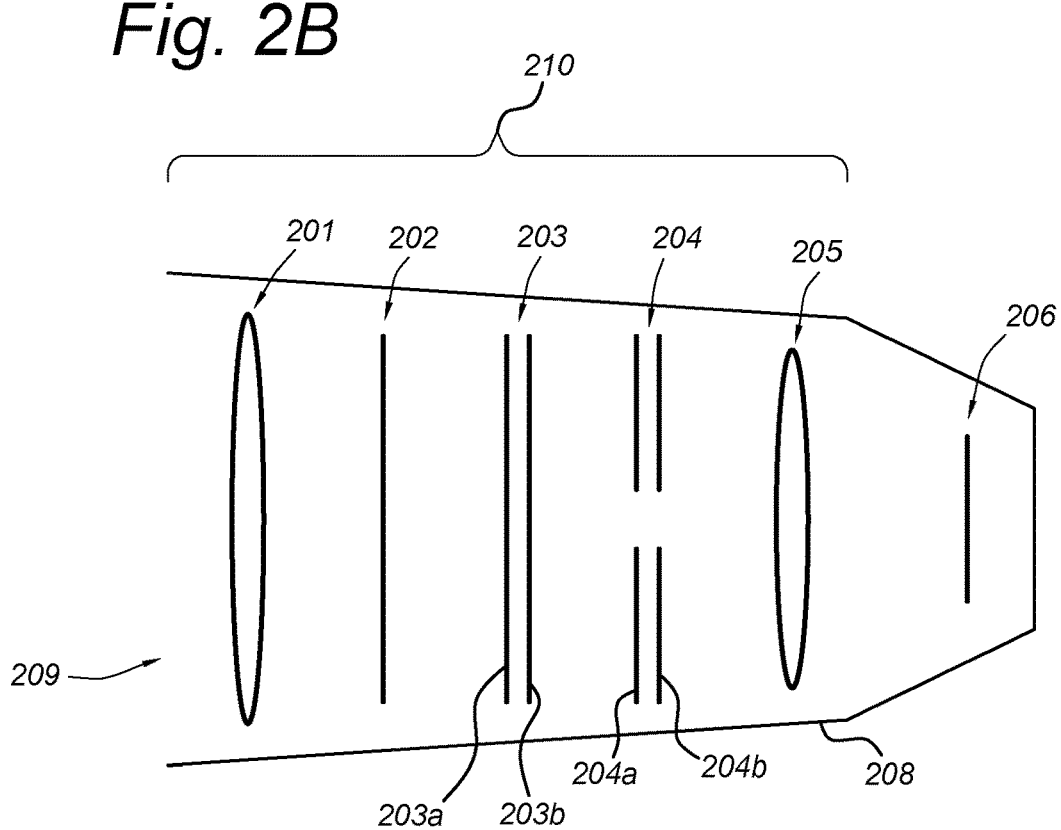
FIG. 2B shows a schematic view of a camera of a head-mounted device including a pair of orthogonally oriented polarizers.

FIG. 2B shows the camera of FIG. 2A, in which the visible light reduction filter 203 has been implemented as a pair of orthogonally oriented polarization filters 203a and 203b. Moreover, the visible light diaphragm 204 has been implemented as a pair of diaphragms 204a, 204b that are made of an orthogonally oriented polarization filter material. For example, such a material comprises an iodine-containing polymer. Such a pair of orthogonally oriented polarization filters is known to transmit about 90% to 95% of the radiation in the near-infrared wavelength range, while removing about 98% to 99% of the visible light in a spectrally linear fashion. It is noted that such an iodine-containing polymer does not remove the visible light entirely. This is in line with the purpose of the filter and diaphragm to remove a lot of the visible light but not all.

Figure 3A:
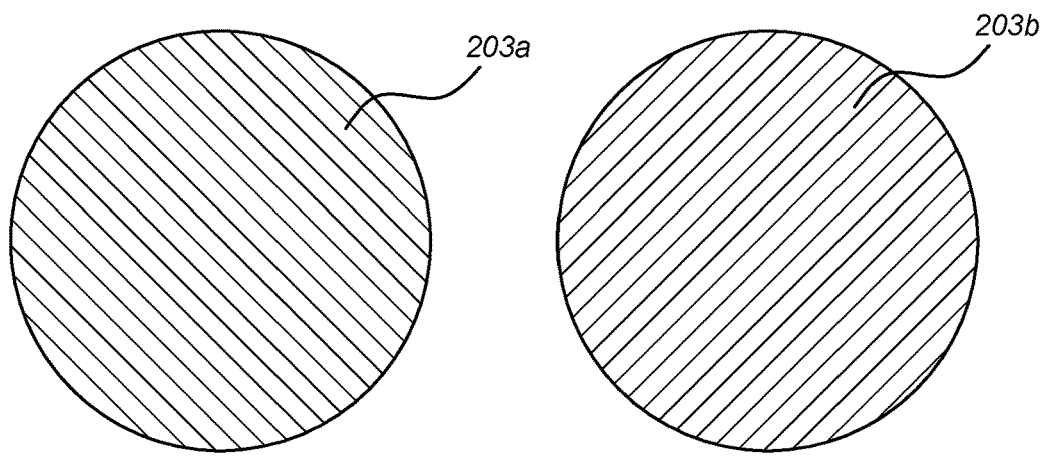
FIG. 3A illustrates a pair of orthogonally oriented polarization filters.

FIG. 3A illustrates the pair of orthogonally oriented polarization filters 203a and 203b in a see-through direction. The diagonal lines indicate a polarization direction. It is noted that the polarization direction of the first filter 203a is orthogonal to the polarization direction of the second filter 203b. It is observed that in certain applications it may be sufficient to provide only one polarization filter instead of two. Moreover, in case two polarization filters are provided, the amount of visible light reduction may be made variable by making the filters 203a and 203b rotatable with respect to each other under control of a control software, for example.

Figure 3B:
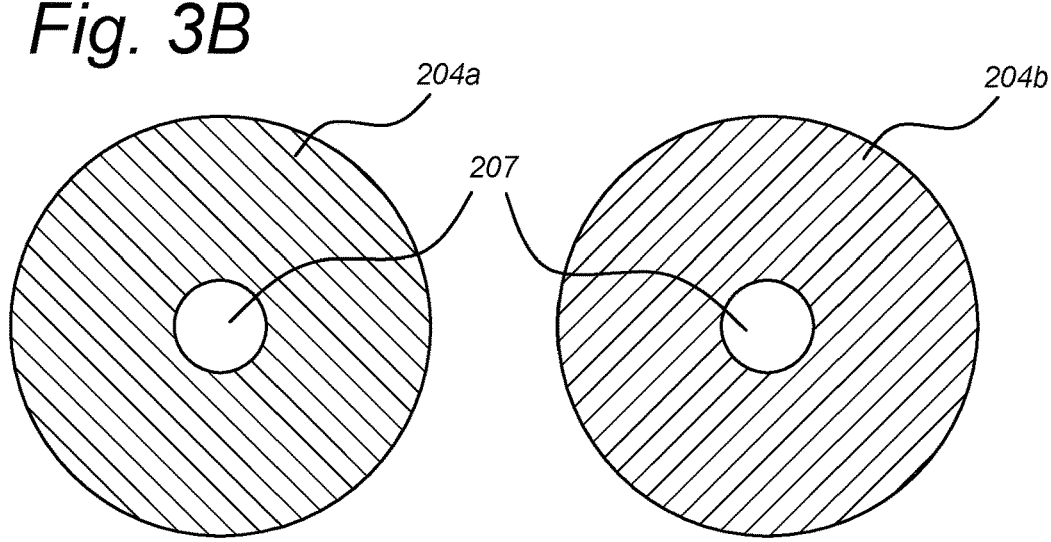
FIG. 3B illustrates a pair of diaphragms, made of orthogonally oriented polarization filters having an aperture.

FIG. 3B illustrates the pair of diaphragms 204a, 204b, made of orthogonally oriented polarization filters having an aperture 207. The diagonal lines indicate a polarization direction. It is noted that the polarization direction of the first aperture filter 204a is orthogonal to the polarization direction of the second aperture filter 204b. It is observed that in certain applications it may be sufficient to provide only one polarization filter-based diaphragm instead of two. Moreover, in case two polarization filter-based diaphragms are provided, the amount of visible light reduction may be made variable by making the aperture filters 204a and 204b rotatable with respect to each other under control of a control software, for example.

Alternatively, certain implementations may comprise one polarizing filter 203a and one polarizing diaphragm filter 204a, omitting either one or both of the second filter 203b and second diaphragm filter 204b. The polarization direction of the one filter 203a may be orthogonal (or have another desired orientation or be variable) with respect to the one diaphragm 204a.

Figure 3C:
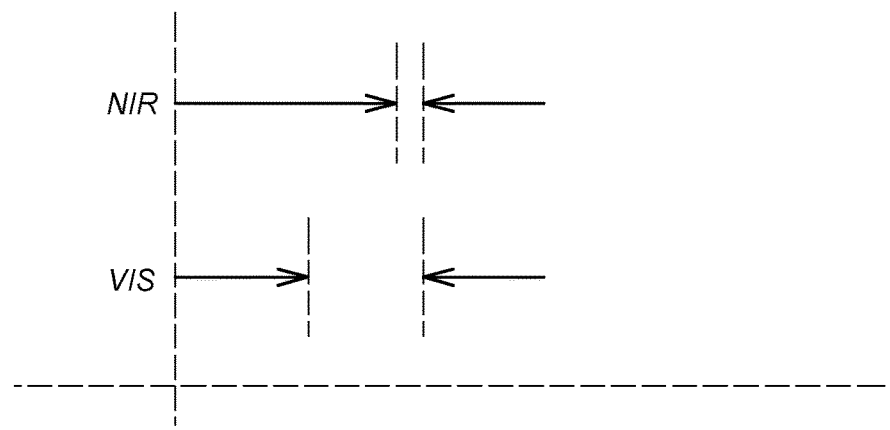
FIG. 3C illustrates an effect of a diaphragm filter.

FIG. 3C illustrates an effect of the diaphragm filter 204. The graph shown in FIG. 3C has the wavelength on the vertical axis and the distance from the camera on the horizontal axis (in an arbitrary scale). Depth of field is the distance between the nearest and the farthest objects, as seen from the camera, that are in acceptably sharp focus in an image. Since the visible light can only pass through the aperture 207 of the diaphragm filter 204, the visible light has a relatively large depth of field, as indicated by the large space in between the arrows in the horizontal line representing a visible wavelength (VIS). However, the invisible light wavelength range that is allowed to pass the material of the diaphragm filter 204, has a relatively small depth of field, as illustrated by the smaller space in between the arrows in the horizontal line representing a near-infrared wavelength (NIR). Since the invisible light may have much less intensity than the visible light, it may be advantageous to keep all the invisible light, while reducing the amount of visible light via the diaphragm filter 204. Moreover, due to dispersion, the focal spot of a lens in respect of different wavelengths differs. To create well-focused image in all detected wavelengths, an expensive and heavy lens system would normally be necessary. The present diaphragm filter creates a large depth of field for the visible light wavelength range, while creating a narrow field of depth for the invisible light wavelength range. This principle may be exploited by optimizing the focus of the lens for the invisible light with the narrow field of depth. This way, the invisible light image is sharp and well-focused. Since the visible light has a large field of depth, the visible light image is also sharp and well-focused. Thus, the system allows a light-weight, high-quality imaging device with a relatively simple lens and filter.

Figure 4:
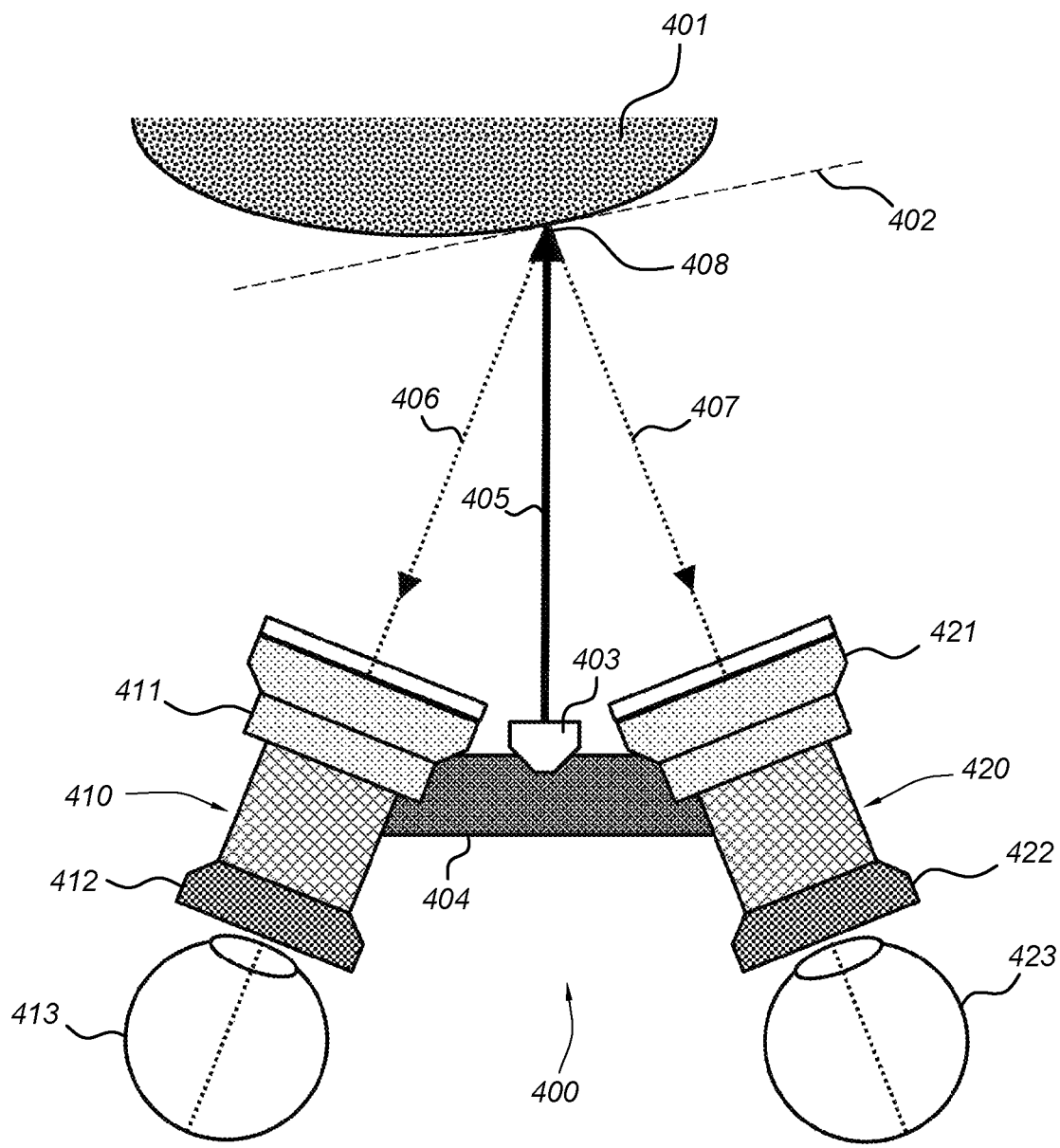
FIG. 4 illustrates an optical principle of stereoscopic viewing using a binocular device.

FIG. 4 illustrates an optical principle of stereoscopic viewing. It shows a binocular device 400. It is observed that the figure is simplified in order to explain the concepts disclosed herein. In many practical embodiments, where the focal point may be further away, for example at a working distance of about 20 centimeters to 1 meter, the line of vision of the left eye 413 may be almost parallel to the line of vision of the right eye 423. So the left optics 410 may be implemented with a very small angle or parallel to the right optics 420.

The binocular device 400 comprises a support structure 404 on which the components of the binocular device 400 are attached. In certain embodiments, the whole device may be encapsulated in a housing. Alternatively, the components of the left image may be encapsulated in a first housing and the components of the right image may be encapsulated in a second housing, both housings being attached to the support structure 404. In either way, the left optics 410 and the right optics 420 are fixed with respect to each other. In certain embodiments the left optics 410 and the right optics 420 may be movable with respect to each other, for example for customizing the device 400 for a particular user.

The binocular device 400 may comprise left optics 410. The left optics 410 may comprise a left camera 411 and a left display 412. The right optics 420 may comprise a right camera 421 and a right display 422. The left camera 411 and right camera 421 may comprise the visible light reduction filter 203 and/or visible light diaphragm 204, as explained above. However, certain embodiments may omit such a filter or diaphragm in one or both of the cameras.

The binocular device 400 may further comprise a light source 403. The light source 403 may be any device that can emit light in a desired wavelength range. Examples of suitable light sources include light emitting diode (LED), incandescent light, halogen light, or another light source. The light source 403 may comprise two or more light sources that generate light of different spectra (for example, a light source that generates white visible light and a light source that primarily generates light of an invisible wavelength range, such as a near-infrared wavelength range), and optics to combine the light produced by these light sources into one bundle. Alternatively, the light source may comprise a single emitter that emits light in both visible and invisible wavelengths. Yet alternatively, the light source 403 may substantially emit only light of the invisible wavelength range. For example, in certain applications it may be assumed that visible light is available in abundance by environmental lighting generated by operation room lights or sunlight, so that no additional visible light needs to be generated by the binocular device 400.

As illustrated in the figure, in operation, the light source 403 generates light. For example, light ray 405 may hit an object 401, such as a tissue to be inspected. This is illustrated by arrow 405. The tangent plane of the tissue at the point of incidence 408 of the light ray 405 with the tissue is illustrated by dotted line 402. In case of a diffuse reflection or fluorescence, for example, light travels from the point of incidence 408 to both the left camera 411, as illustrated by arrow 406, and to the right camera 421, as illustrated by arrow 407.

Figure 5:
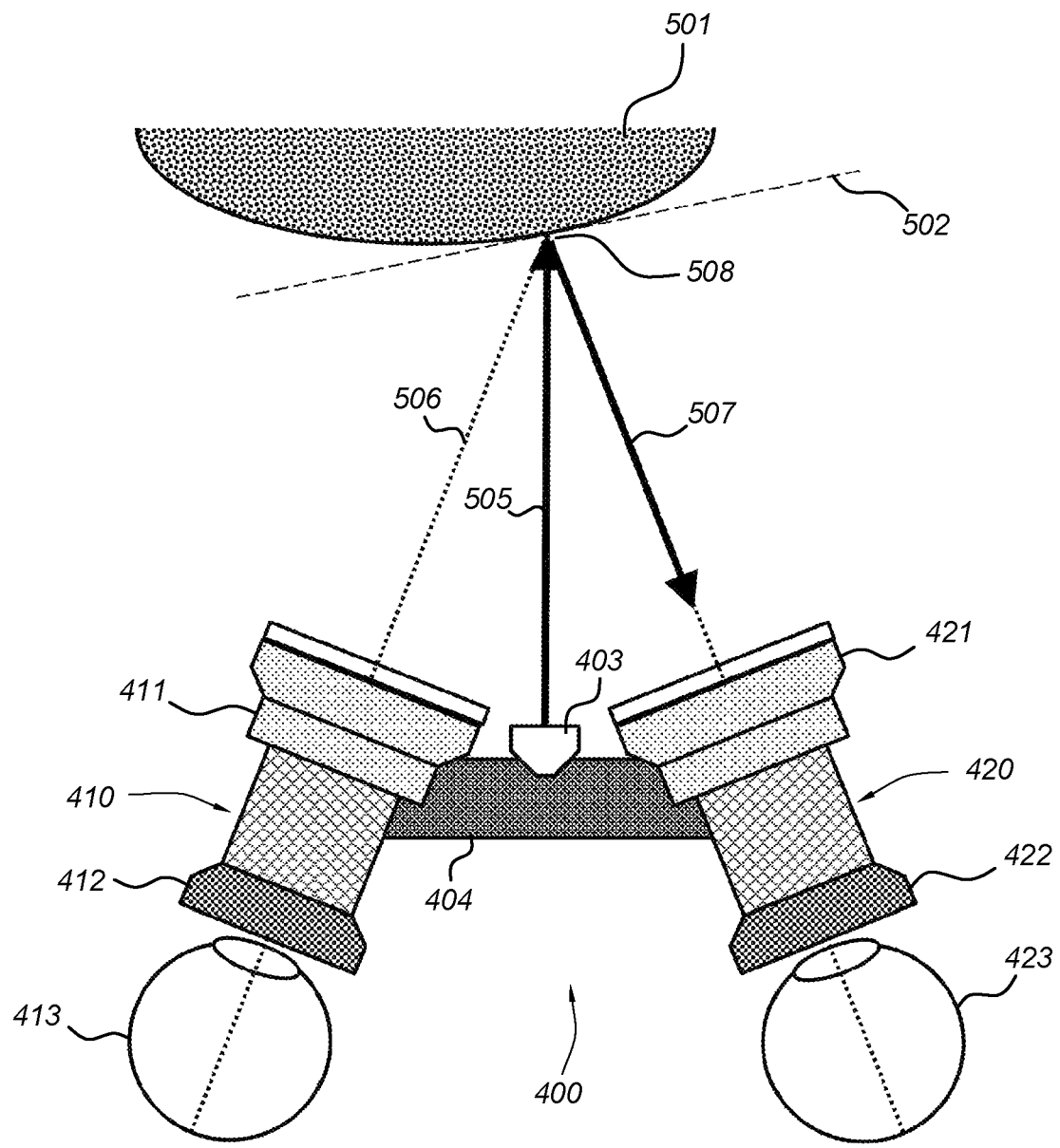
FIG. 5 shows a first example of a specular reflection.

FIG. 5 shows the binocular device 400 in case of a specular reflection by tissue 501 at point of incidence 508 with tangent plane 502. The light ray 505 emitted by the light source 403 is reflected mostly towards, in the present example, the right camera 421 along ray 507. Only little to none of the light is reflected to the left camera 411, as indicated by dotted line 506.

Figure 6:
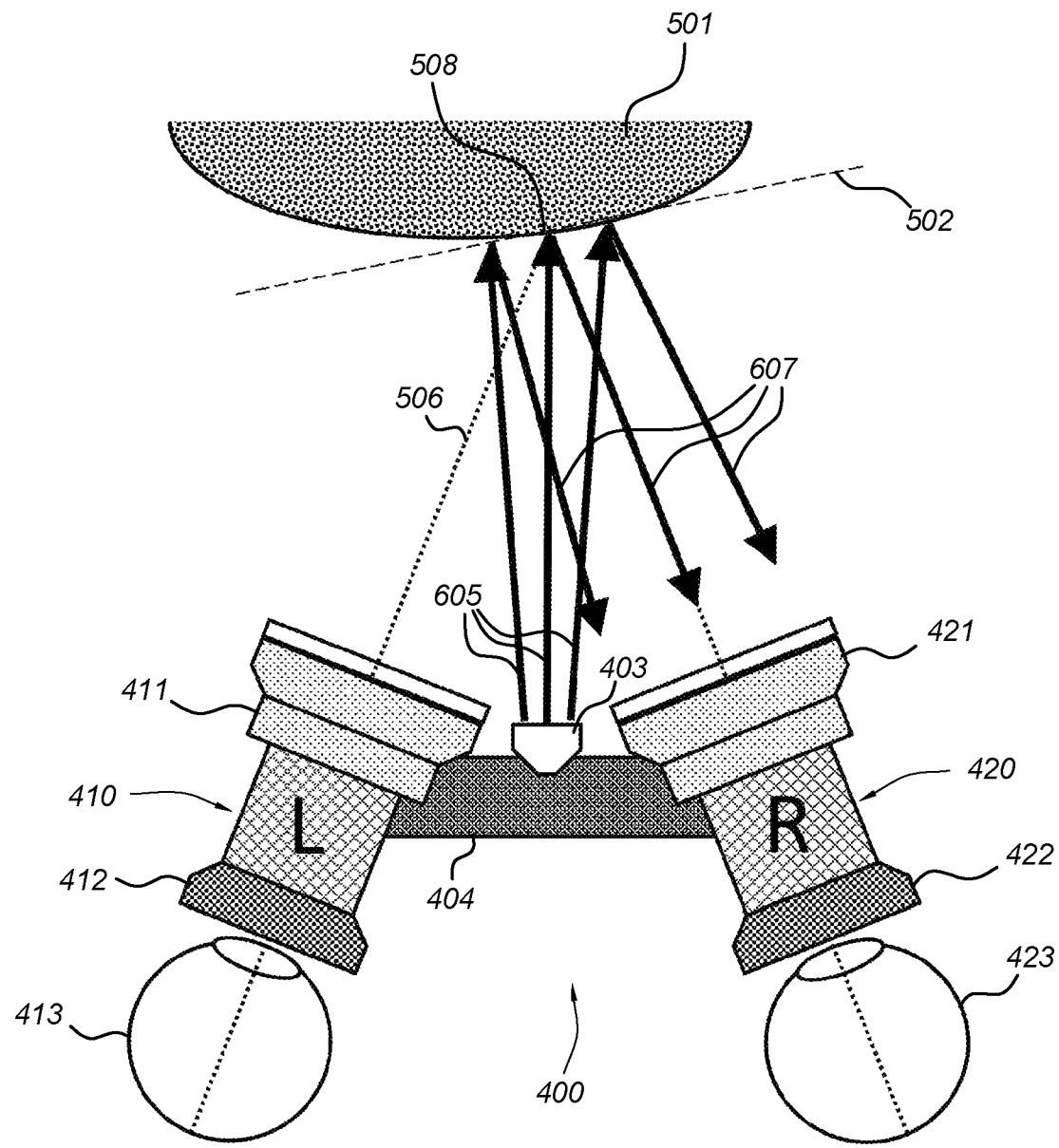
FIG. 6 shows a second example of a specular reflection.

FIG. 6 shows that, of course, there is not just one light ray but a light bundle 605 that is reflected in a bundle 607 into the right camera 421. The geometrical beam shape generated by the light source 403 in respect of the visible wavelength range may be, as much as possible, identical to geometrical beam shape generated by the light source 403 in respect of the non-visible wavelength range.

Figure 7:
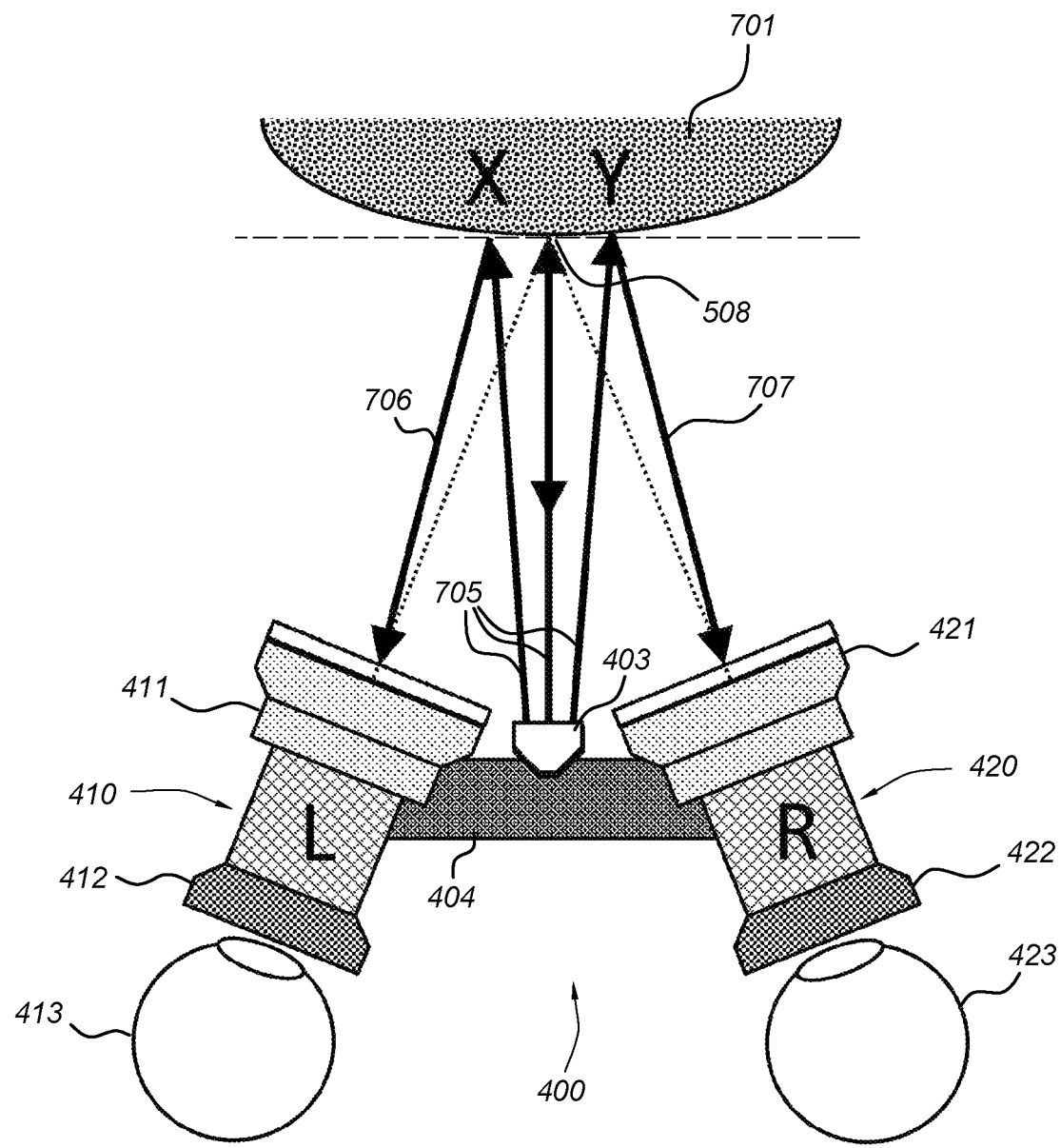
FIG. 7 shows a third example of a specular reflection.

FIG. 7 illustrates another example of specular reflection, wherein a part 707 of the light bundle 705 emitted by the light source 403 is reflected by the tissue 701 towards the right camera 421 and another part 706 of the light bundle 705 is reflected towards the left camera 411.

It would be undesirable if specular reflections would be mistakenly recognized by the user as actual diffusely-reflecting contrast or fluorescence originating from tissues. In the case that both cameras receive off-axis specular reflections, the output image could be mistakenly recognized as, for example, NIR-induced fluorescence from two separate spots (X & Y in FIG. 7) on the tissue surface. The VIS light source may be kept continuously on (to avoid visible flicker). The dichroic diaphragm and/or filter may suppress specular reflections in the visible wavelength much stronger than NIR ones. The NIR source can be modulated ON/OF without causing visible flickering. Images may be captured by the cameras 411 and 421 while the NIR light source is on and while the NIR source is off. The resulting pairs of images (one pair (left/right) with the NIR light source on and one pair with the NIR light source off) may be processed to enhance the NIR visualization. For example, the images obtained with the NIR light source off may be subtracted from the images obtained with the NIR light source on. This way, an image with enhanced visualization of the NIR is created. The NIR image may be converted to a visible color and blended into the image that was obtained with the NIR light source off, so that a combined visualization of the visible light and the NIR light is created. This combined visualization may be displayed on the left display 412 and right display 422. However, it is also possible to display the visible-light only images on the left display 412 and right display 422, without visualization of the NIR light.

As a special imaging mode, the visualization of the NIR light in the left and right displays 412, 422 is alternated. That is, for a certain time period the left NIR image is shown in the left display 412, after that the display of the left NIR image is stopped and the right NIR image is shown in the right display 422 for the certain time period. The time period may be, for example, just long enough for an average human to perceive the flickering. A longer time period is also possible. This visualization mode allows to distinguish a specular reflection from diffuse reflection and fluorescence. In case of a spot caused by diffuse reflection or fluorescence, truly originating from the tissue, the spot will appear at the same location in both left visualization and right visualization, as illustrated in FIG. 4. In case of a spot caused by specular reflection, however, the spot will appear either in only one eye, as illustrated in FIG. 5 and FIG. 6, or at different locations in the left visualization and right visualization, as illustrated in FIG. 7. Thus, in case a spot does not occur at the same location in both eyes (flickers and/or "dances"), the user knows there is a specular reflection and move his or her head, and thereby the cameras of the head-mountable device, to remove the specular reflection from sight.

Another signature of specular reflection versus true tissue contrast or fluorescence is that specular reflections move their position with the head orientation of the observer whereas true contrast and or fluorescence stays on the same place on the tissue.

The visual effect of specular reflections illustrated in FIGS. 4 to 7 may be employed to detect specular reflections in the captured images by means of automated image processing. It is observed that specular reflections may be undesirable, because they may obscure the actual signals, in particular in the invisible wavelength range (e.g., near-infrared range), the signal that is important is the diffuse reflection and/or fluorescence. Specular reflections of the light emitted by the light source 403 would render the diffuse reflections and/or fluorescence invisible. After a left image and a right image have been captured, substantially simultaneously, by the left camera 411 and the right camera 421, with the NIR light source switched on, a specular reflection detection processing may be performed. For example, a comparison between the left image and right image, which have been captured simultaneously, may be performed to detect a particularly bright spot. For example, if the intensity at a certain location in an image is above a certain threshold, a bright spot may be detected. Moreover, if such a bright spot is detected in a first one of the left image and right image, it may be determined whether a bright spot is present in a corresponding location in the other one of the left image and right image. It may be determined whether a bright spot is present in the corresponding location, by comparing the image intensity at the corresponding location to a predetermined threshold, for example. 'Corresponding location' may mean within a certain distance from the same location as the bright spot in the first image. This distance may be determined while taking into account that the corresponding locations of a visualized item may be slightly different in the left image and right image, according to the disparity of objects in the stereoscopic pair of images.

Alternatively, a known algorithm may be employed to estimate the disparity, and the corresponding location in the other one of the left image and the right image, may be determined based on the estimated disparity.

For example, if a bright spot is detected in corresponding locations in the left image and right image according to an estimated disparity, it may be decided that this is not a specular reflection, but just a relatively intense diffuse reflection, as illustrated in FIG. 4.

For example, in case the bright spot is detected in only one of the left image and the right image, but not at the corresponding position in the other one of the left image and the right image, it may be decided that it is a specular reflection, as shown in FIGS. 5 and 6.

For example, if a bright spot is detected in differing locations just offset from two corresponding locations in the left image and right image according to an estimated disparity, it may be decided that the bright spot is a specular reflection in both images, as shown in FIG. 7.

Preferably, the specular reflection detection is performed for the non-visible channel (e.g., the NIR channel), because the specular reflections in that channel may not be reduced by the visible light filter and/or visible light diaphragm, and it may be vital to properly visualize low-intensity features in the non-visible wavelength band. Alternatively, the specular reflection detection may be performed for each color channel (red, green, blue, non-visible light) separately. Yet alternatively, the intensity of the channels may be combined to detect reflections for all detected wavelength ranges at the same time.

When a specular reflection has been detected, an alarm signal may be generated to indicate a specular reflection is detected. The alarm signal may comprise, for example, a sound signal or a visual indication. The visual indication may be shown on the displays 412, 422. For example, the detected specular reflection in the non-visible wavelength range may be displayed in a different color than the remainder of the non-visible wavelength image overlay. For example, the non-visible wavelength may be shown generally as a green overlay on top of a color image of the visual wavelength ranges. However, if a spot is identified as a specular reflection, the spot may be shown as a darker green as the remainder of the green overlay. This allows the user to move the viewing position a bit, to a position where there is no specular reflection.

Alternatively, the detected specular reflection may be removed by image processing. For example, the image intensity at the bright spot may be locally reduced by multiplying the intensity values by a reduction factor, so that the image intensity at the bright spot is made to be of the same average level as the average image intensity around the bright spot.

In certain embodiments, neither of the cameras is sensitive to radiation in an invisible wavelength band of radiation. For example, both cameras may be sensitive to radiation in a visible light wavelength band of radiation (for example, in case of color cameras, a red wavelength range, a green wavelength range, and a blue wavelength range). The visible light reduction filter 203 and the visible light diaphragm 204 may be omitted as well, as disclosed hereinabove.

The binocular device may optionally comprise a processing unit configured to: receive a signal representing a left image from the left camera and a right image from the right camera, the left image and the right image being captured substantially simultaneously by the left camera and the right camera, respectively; compare the left image to the right image; and detect a specular reflection based on a result of the comparison.

In an optional particular visualization mode, the binocular device may alternatingly show a left image based on the left video signals generated by the left camera on the left display and a right image based on the right video signals generated by the right camera on the right display, to allow a user to distinguish a specular reflection. A specular reflection can be easily identified by comparing the left and right image, as a specular reflection will dance back and forth as the images are compared whilst fluorescence and diffuse reflections will remain static for both cameras. This visualization mode allows to distinguish a specular reflection from diffuse reflection and/or fluorescence.

The device may detect, suppress, or make known to the user specular reflections within various parts of the optical spectrum.

Figure 8:
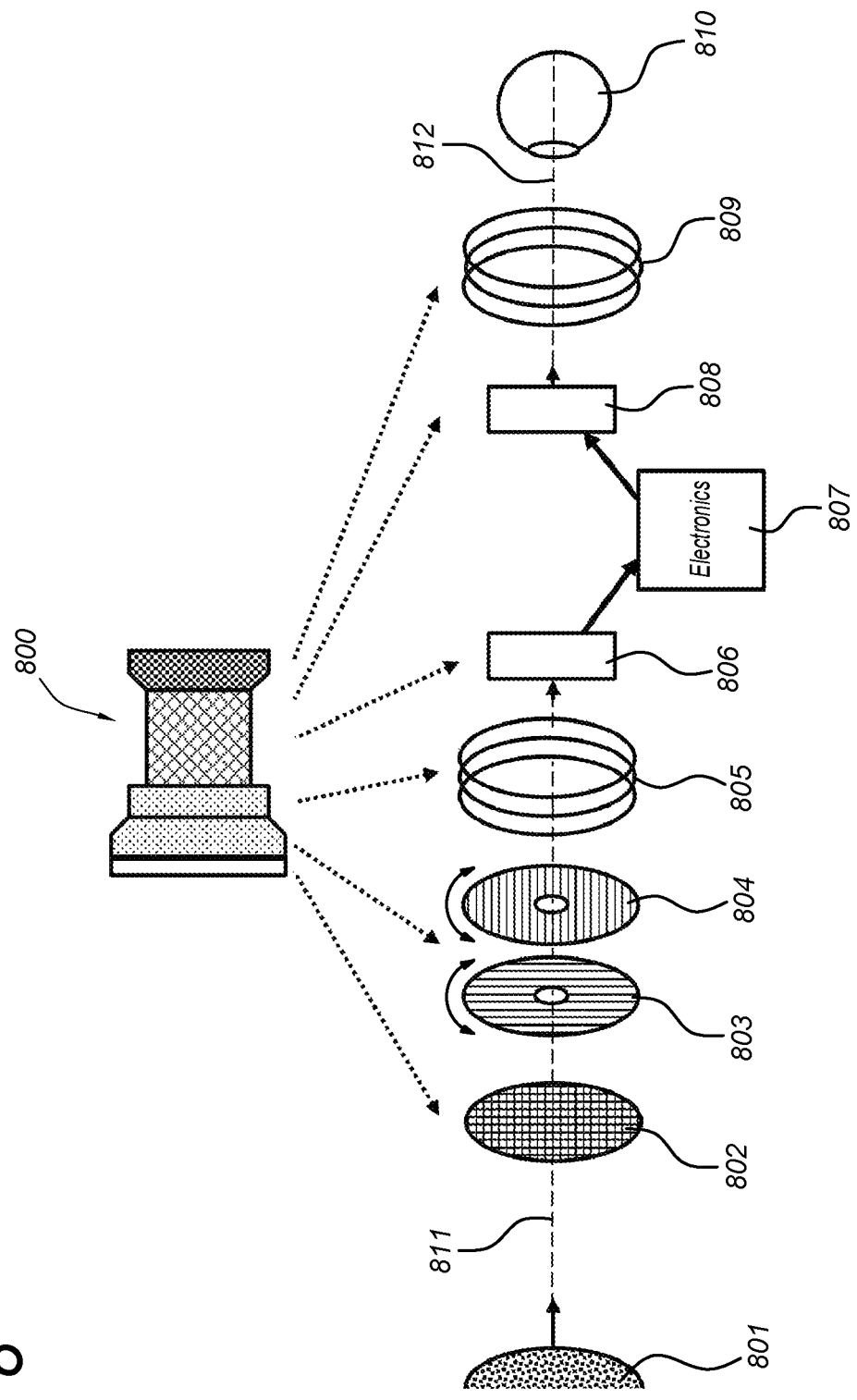
FIG. 8 shows a diagram of a combined camera and viewer for one eye.

FIG. 8 shows a view of a combined camera and viewer 800 for one eye (left optics or right optics). In use, the device 800 may be fixed in between an eye 810 of the observer and an object, for example a tissue, 801, to be observed. In typical use the device 800 may be held or attached close to the eye 810, and at a working distance from the object 801 to be observed. The device 800 may comprise input optics including a notch filter 802, a dichroic diaphragm, which may be implemented as shown as a pair 803, 804 of polarization filters, an optics set 805, which may comprise one or more lenses and other optical elements. The order of these components may vary depending on the implementation. The device 800 further comprises an image sensor 806, for example a CMOS chip or another type of camera chip. For example, the chip may have a surface that converts radiation projected thereon in both the visible wavelength band of radiation and the invisible wavelength band of radiation into an electronic signal. The image sensor 806 is electrically connected or connectable to electronics 807 for processing the image signals generated by the image sensor 806. This electronics 807 may be incorporated in the binocular device 101, or alternatively, may be implemented in an external processing device, such as a wearable computer 102 that has sufficient processing power. This helps to keep the head-mountable display light-weight.

The device 800 further comprises a micro display 808 for displaying processed images based on image signals that are output by the electronics 807 and transmitted to the micro display 808. The micro display may have, for example, a size comparable to an eye. The size of the micro display may be arbitrary, as the device 800 further comprises output optics, including ocular display set 809, to project the image output by the micro display 808 onto the retina of the eye 810. The input optics 802, 803, 804, 805, and image sensor 806 may be optically isolated from the micro display 808 and output optics 809, for example by disposing them in two separate compartments with walls that are not transmissive to radiation of the wavelengths concerned.

In the embodiment shown, the input optics, camera, micro display, and output optics are in line, that is, share the same optical central axis 811, 812. This way, the user has the impression as if looking straight ahead, through e.g. a pair of binoculars. Thus, it is easy for the user to orient himself and his/her hands with respect to the images produced by the micro display 808. In alternative embodiments, there may be an inclination between the central 811 axis of the input optics and camera 806 on the one hand, and the central axis 812 of the micro display and output optics, on the other hand. For example, the input axis 811 may be inclined a little downwards with respect to the output axis 812.

Figure 9:
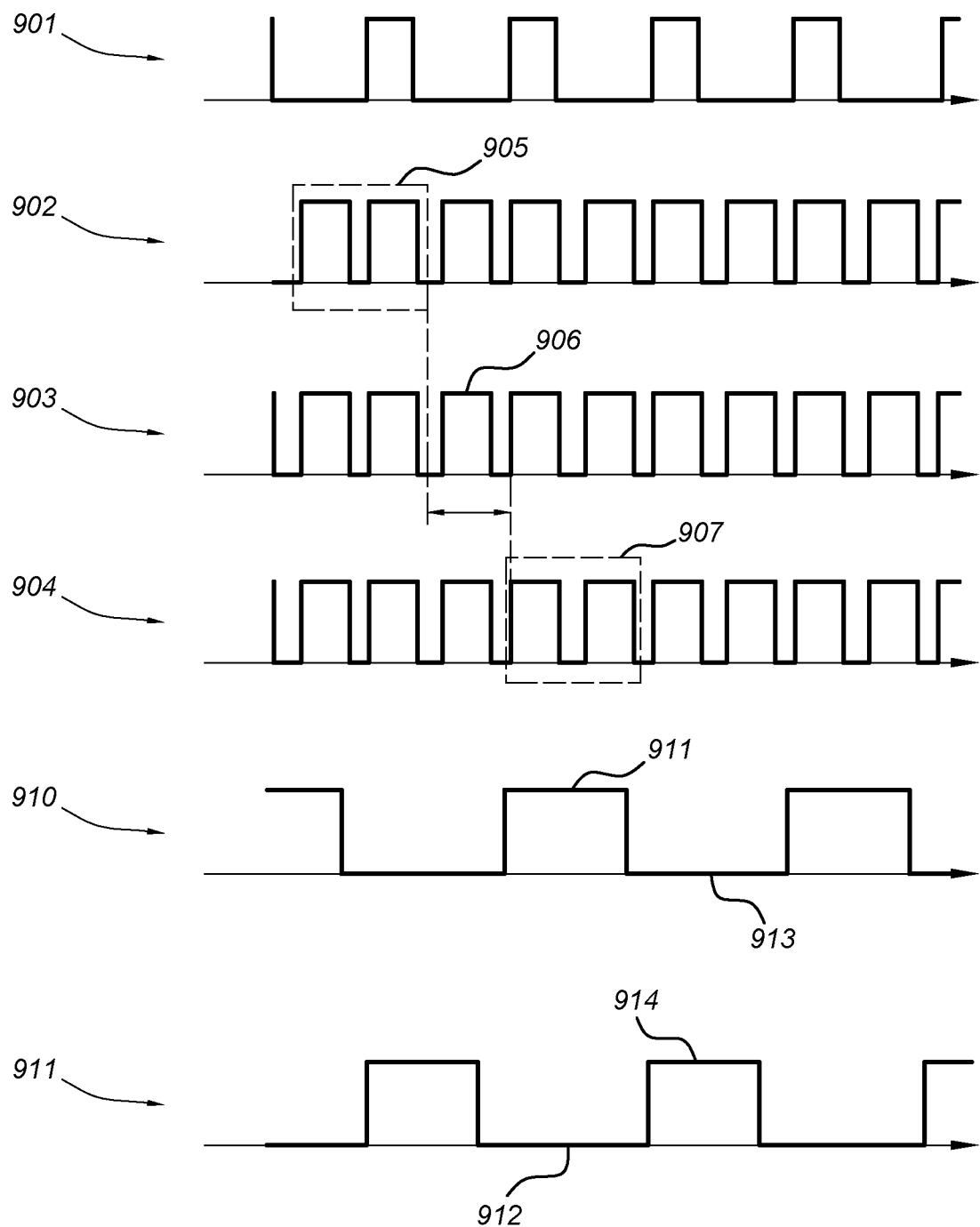
FIG. 9 shows an example of a timing diagram of the binocular device in operation.

FIG. 9 shows an example of a timing diagram of the binocular device 400 in operation. The timing graphs show time on the horizontal axis, and the performing of a certain activity on the vertical axes (a high position means an action is performed). It is observed that the camera may be configured to capture images at a certain frame rate, as indicated in graph 902.

The light source 403 may have separately controllable visible light and non-visible light generating capabilities. Alternatively, the light source may generate only the non-visible light. In that case, visible light may be provided from elsewhere. However, for reasons of consistency between the images recorded, it may be preferable to have a single light source that can generate both visible and non-visible light in a single light bundle. Moreover, to prevent visible flickering, the visible light source may be kept continuously emitting radiation while the non-visible light is switched on and off alternatingly. This prevents flickering not only for the camera images, but also for any other people in the room that do not have a binocular device 400.

The non-visible light may be generated by the light source in stroboscopic fashion. This is illustrated in graphs 901 and 902. The light source for non-visible light, such as NIR light, may be configured to flash at a lower speed than the frame rate, for example at half the frame rate, so that while capturing each first frame the non-visible light source is off, and while capturing each second frame, the non-visible light source is on. One image may be taken with the non-visible light source switched off. The next image may be taken with the non-visible light switched on. Thus, two successive images produce a result of imaging without non-visible light, and a result of imaging with non-visible light, as indicated at 905. After such a pair of images has been captured from each camera, the processing electronics 807 may calculate an output image based on the pair of captured input images, as indicated at 906 in graph 903. The output image may be displayed by the micro display 808 as soon as the processing in block 906 has been completed, as indicated at 907 in graph 904. It will be understood that this is only an example timing diagram. Other timings and other order of steps may be implemented alternatively.

For example, in the processing step 906, the processing electronics 807 may subtract the image with the non-visible light source switched off from the image with the non-visible light source switched on. This way, the visible light is subtracted, so that the non-visible light is enhanced in the subtraction image. Thus, if a pixel in the image with the non-visible light source switched off has a value X, and the same pixel in the image with the non-visible light source switched on has a value Y, the same pixel in the subtraction image would have the value Y−X. The pixels of the subtraction image that are larger than a predetermined threshold may be blended, in a predetermined visible color, on top of the image that was captured with the non-visible light source switched off.

Moreover, a speckle detection mode may be provided, in which the user may detect speckle by means of a visual effect. For example, the specular reflections may be indicated by means of an alarm or a visual indication. Alternatively, in the speckle detection mode, illustrated by graphs 910 and 911, the overlay visualization of the non-visible light image is shown alternatingly on only the left display 412, during a first time interval 911, 912, and on only the right display 422, during a second time interval 913, 914. In such a case, the viewer can assess if there is a specular reflection in the non-visible domain, by considering if there is a spot that appears to be oscillating between two positions. The time intervals 911,912 and 913,914 may be made longer or shorter as desired, for example using a time interval that is at least as long or longer than the time interval in which two images are captured (at 905), to ensure that the flickering is visible to a human observer.

Figure 10:
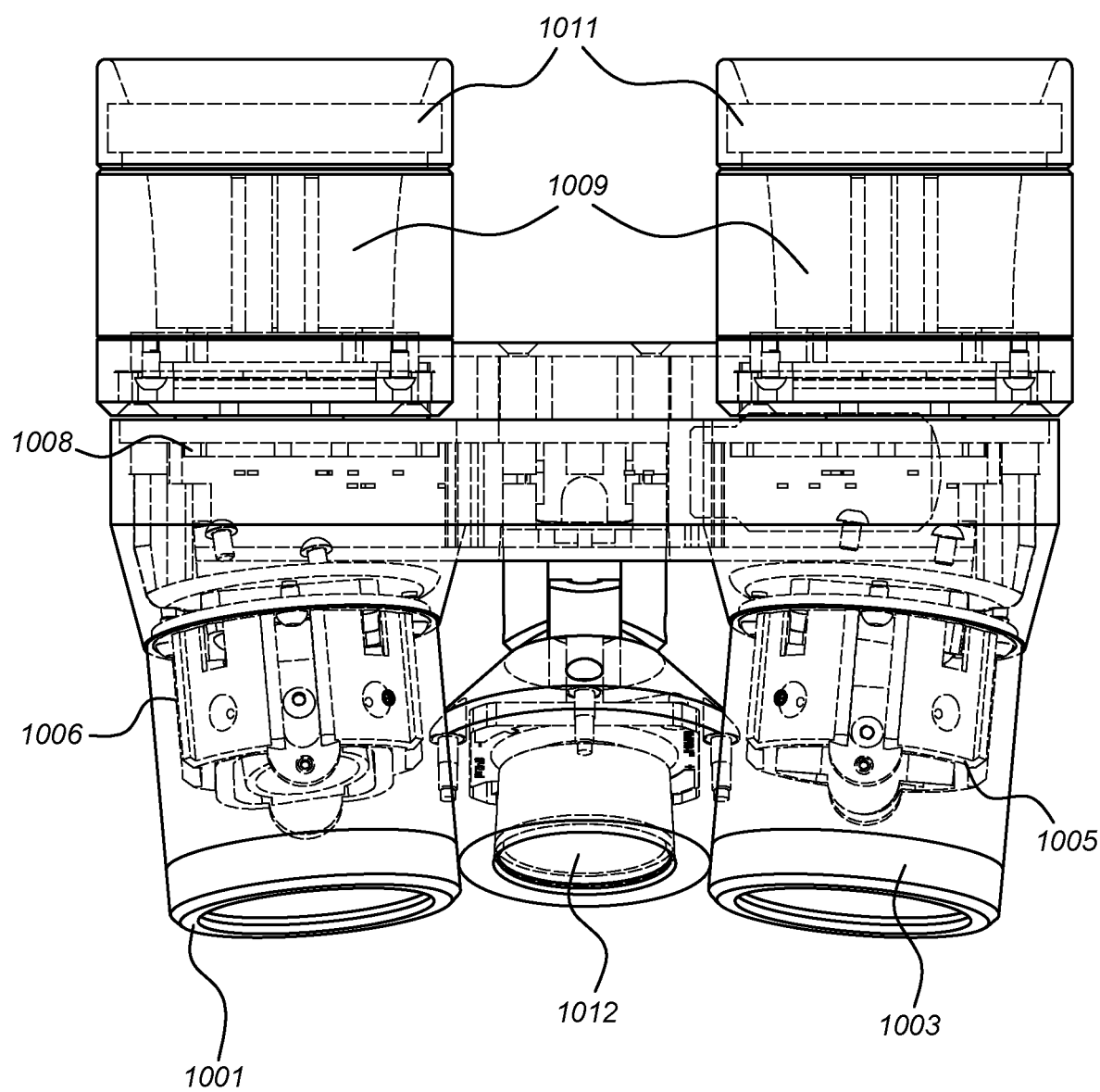
FIG. 10 shows a partly worked open view of an exemplary head-mountable binocular device, viewed from below.
Figure 11:
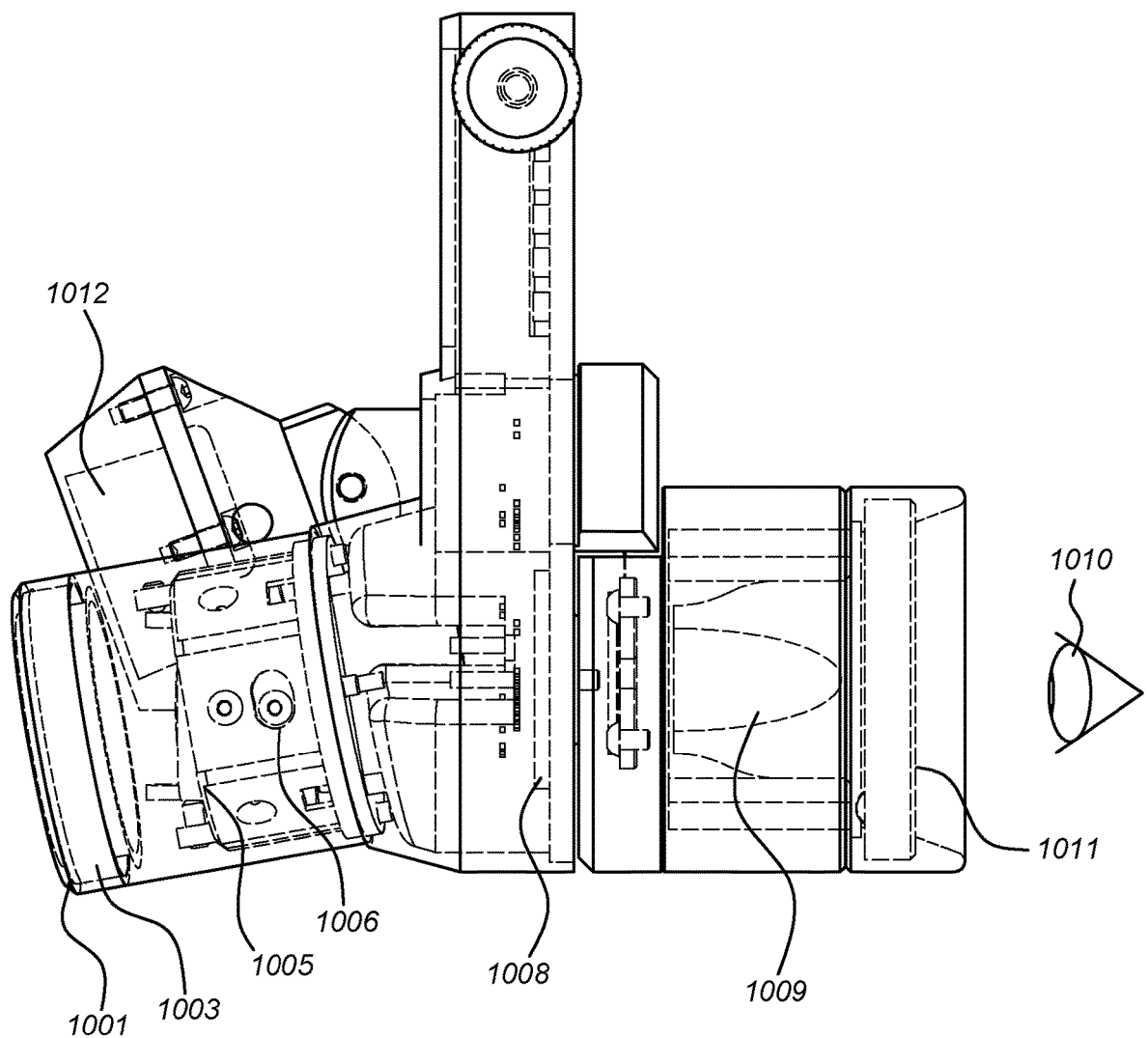
FIG. 11 shows a partly worked open view of the same head-mountable binocular device, viewed from aside.

FIG. 10 shows a partly worked open view of an exemplary head-mountable binocular device, viewed from below. FIG. 11 shows a partly worked open view of the same head-mountable binocular device, viewed from the side. In this example, the optical central axis of the left viewing portion is substantially parallel to the optical central axis of the right viewing portion. Moreover, the optical axis of the left camera portion and the optical axis of the right camera portion are slightly inclined towards each other and downwards. However, the alignment of the optical axes is not a limitation.

Shown in FIGS. 10 and 11 are the camera part comprising the optional notch filter 1001, the visible light diaphragm 1003, the camera lens 1005, the camera sensor, or image sensor, 1006. Moreover, shown in FIGS. 10 and 11 are the display part comprising the micro display 1008, output optics 1009, and eye piece 1011, which comprises an annular structure suitable for holding close to the eye 1010. Moreover, shown in FIGS. 10 and 11 is the light source 1012. These items have been described in greater detail hereinabove, and therefore their properties are not repeated here.

Figure 12:
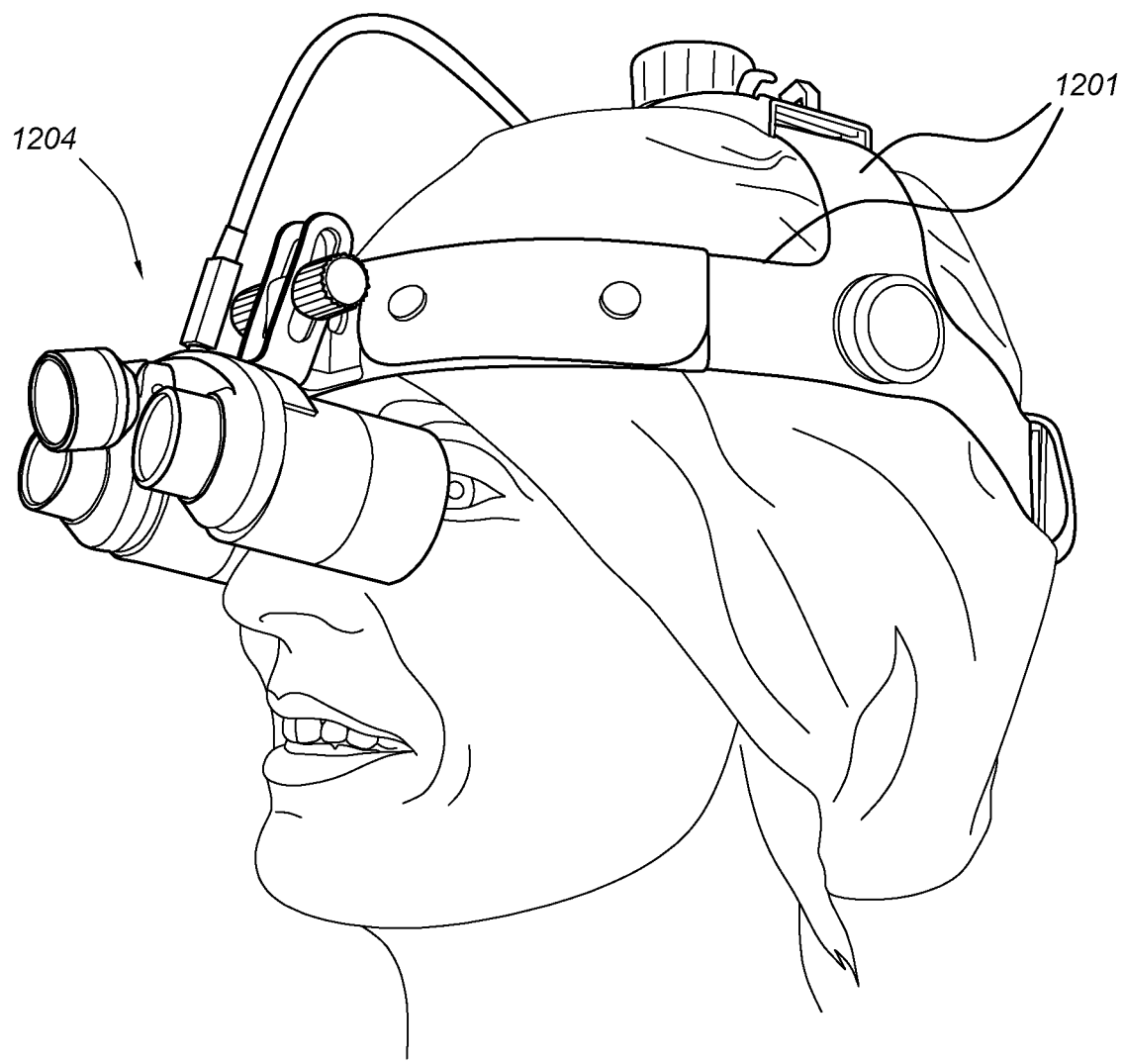
FIG. 12 shows a head-mountable device attached to the head of a user.

FIG. 12 shows how the head-mountable device can be attached to the head of a user, by means of at least one strip 1201 connected to the support structure 1204 that can be fitted around the head. The eyepieces may be aligned to the eyes of the user, as shown.

Figure 13:
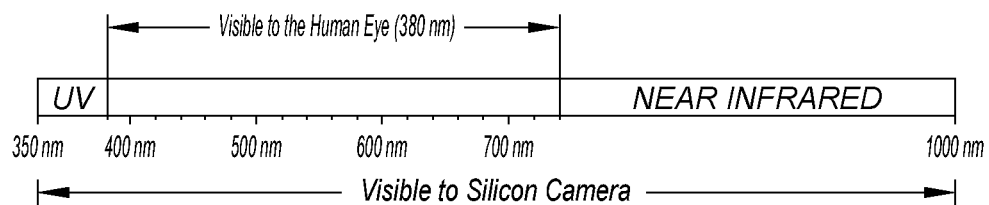
FIG. 13 shows several wavelength bands.

FIG. 13 shows several wavelength bands of visible light and invisible light (ultraviolet and near-infrared), in nanometers (nm). It is noted that blue may be centered around 445 a nanometer wavelength, green may be centered around a 535 nanometers wavelength, and red may be centered around 575 nanometers wavelength. Ultraviolet may be considered to be radiation with a wavelength below around 380 nanometers. Near-infrared may be considered to be radiation in a wavelength range from about 740 nanometers up to about 1000 nanometers. Infrared radiation goes further beyond 1000 nanometers. It is noted that these wavelengths are provided purely as illustrative examples. The devices described herein may be designed for different wavelengths for detection, processing, and visualization.

Figure 14:
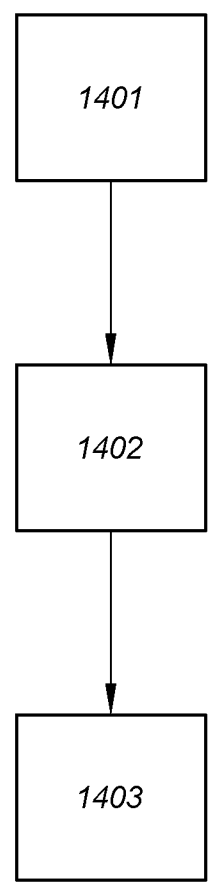
FIG. 14 shows a flowchart of a method of visualizing visible and invisible radiation.

FIG. 14 shows a flowchart of a method of visualizing visible and invisible radiation. The method comprises, in step 1401, receiving radiation, about a same field of view along respective left and right input optical axes, by left and a right input optics coupled to a support structure, and transmitting the light onto a left image sensor of a left camera and a right image sensor of a right camera, respectively, the left camera and the right camera being coupled to the support structure, wherein at least one of the cameras is sensitive to both radiation in an invisible wavelength band of radiation and radiation in a visible light wavelength band of radiation, wherein the input optics of the camera that is sensitive to the invisible wavelength band of radiation is transmissive for the invisible wavelength band of radiation and reductive for the visible light wavelength band of radiation. The method further comprises, in step 1402, creating left and right video signals from the detected radiation received by the left camera and the right camera, respectively. The method further comprises, in step 1403, presenting, by a left display and a right display coupled to the support structure and to be viewed by a pair of eyes of a user through a left eyepiece operatively connected to the left display and a right eyepiece operatively connected to the right display, left and right video images formed with visible light based respectively on the left and right video signals.

It may be observed that the features for reduction of specular reflections may be implemented in a binocular device, even in absence of the reduction of visible light. That is, the visible light filter 202 and the visible light diaphragm 204 may both be omitted in a device or method that includes the image processing functionality of detecting a specular reflection.

Certain embodiments comprise a head-mountable device, or a binocular device that is designed to be held directly in front of the eyes, which device has at least one camera and/or light source, to observe the object from a working distance in an open space (e.g., an indoor or outdoor environment). In contrast, other applications, such as endoscopy, may operate in a largely dark cavity in which lighting can be controlled freely. This open space poses some constraints on the lighting. First, there is the presence of environmental light caused by external light sources. Second, it may not be possible to optimize the lighting conditions purely for the cameras of the binocular device, because other people and/or other camera equipment should preferably not be disturbed by the lighting caused by the binocular device. The techniques disclosed herein may help to improve the usability of the binocular device under these circumstances. For example, the cameras of the binocular device may be equipped with a high dynamic range, high quality optics, special image processing techniques, and/or polarizing filters, dichroic filters, polarizing diaphragms, and/or dichroic diaphragms, as described herein. For this reason also, the light source of the binocular device may be configured to keep the emitted light in the visible wavelength band as much as possible constant, not to disturb any people around. As described above, the emitted light in the invisible wavelength band may be flashing in stroboscopic fashion, so that images of visible light can be combined with images with invisible light. Since the flashing occurs in the invisible wavelength band, this does not disturb the people around.

Although several techniques have been disclosed hereinabove in relation to a head-mountable binocular device, this is not a limitation. It is observed that the features of a image processing techniques, and/or polarizing filters, dichroic filters, polarizing diaphragms, and/or dichroic diaphragms, may also be applied to a camera in general.

According to another aspect, a camera comprises input optics and an image sensor, the image sensor being configured to create a video signal from detected optical radiation received from the input optics about a field of view along an input optical axis, at least one of the cameras being sensitive to both radiation in an invisible wavelength band of radiation and radiation in a visible light wavelength band of radiation, the input optics being transmissive for the invisible wavelength band and reductive for the visible light wavelength band. Such a camera may be designed for many different uses, such as, for example, endoscopy.

Optionally a display is configured to present a video image, formed with visible light by the display, based on the video signal.

Optionally, the display is arranged to be viewed by a user through an eyepiece operatively connected to the display.

The input optics of the camera may comprise a polarizing filter comprising at least one layer of a polarizing material.

The polarizing filter may comprise at least two layers of the polarizing material, having a mutually orthogonal polarization direction.

The device may comprise a light source coupled to the camera by a support structure, the light source being capable of generating radiation within at least the invisible wavelength band and the visible light wavelength band, wherein the light source is configured to generate beams of emitted visible light and invisible radiation that are aligned to be substantially identical in geometrical shape and position.

The device may comprise a light source coupled to the support structure, capable of generating radiation within at least the invisible wavelength band and the visible light wavelength band, wherein the light source further comprises a polarizing filter configured to polarize the visible light within the visible light wavelength band output by the light source and transmit the radiation in the invisible wavelength band, wherein a polarization direction of the polarizing filter of the light source is substantially orthogonal to a polarization direction of the polarizing filter of the input optics.

The input optics may comprise a diaphragm having an aperture, the diaphragm around the aperture being reductive for light in the visible light wavelength band, while the diaphragm is transmissive for the light in the infrared wavelength band.

The input optics may comprise a lens with autofocus, wherein the autofocus is configured to bring into focus the radiation in the invisible wavelength band.

The input optics of the camera may comprise a filter that is reductive for the light in the visible light wavelength band in addition to the diaphragm.

The input optics of the camera may comprise a filter comprising iodine for selectively reducing the radiation in the visible light wavelength band.

The device may comprise a light source coupled to the camera by a support structure, for generating at least invisible light and visible light, wherein the light source is configured to intermittently emit the invisible light while keeping the visible light intensity substantially constant, wherein the camera is configured to capture at least one image with the emitted invisible light and at least one image without the emitted invisible light.

The device may comprise a processing unit configured to calculate an enhanced invisible-light image based on the captured image with the emitted invisible light and the captured image without the emitted invisible light.

The image sensor may comprise a sensor die that is sensitive to both the infrared wavelength band of radiation and the visible wavelength band of radiation, wherein the sensor die is configured to output the video signal corresponding to both the radiation in the infrared wavelength band and the radiation in the visible wavelength band.

Some or all aspects of the invention may be suitable for being implemented in form of software, in particular a computer program product. The computer program product may comprise a computer program stored on a non-transitory computer-readable media. Also, the computer program may be represented by a signal, such as an optic signal or an electro-magnetic signal, carried by a transmission medium such as an optic fiber cable or the air. The computer program may partly or entirely have the form of source code, object code, or pseudo code, suitable for being executed by a computer system. For example, the code may be executable by one or more processors.

The examples and embodiments described herein serve to illustrate rather than limit the invention. The person skilled in the art will be able to design alternative embodiments without departing from the spirit and scope of the present disclosure, as defined by the appended claims and their equivalents. Reference signs placed in parentheses in the claims shall not be interpreted to limit the scope of the claims. Items described as separate entities in the claims or the description may be implemented as a single hardware or software item combining the features of the items described.

Certain aspects are defined in the following clauses.

Clause 1. A binocular device for visualizing visible and invisible radiation, comprising
  a support structure;
  a left camera and a right camera coupled to the support structure, the left camera comprising left optics and a left image sensor, the right camera comprising right optics and a right image sensor;
  the left image sensor and the right image sensor being configured to create left and right video signals from detected optical radiation received from the corresponding left and right input optics about a same field of view along respective left and right input optical axes,
  at least one of the cameras being sensitive to both radiation in an invisible wavelength band of radiation and radiation in a visible light wavelength band of radiation, the input optics of said at least one of the cameras being transmissive for the invisible wavelength band and reductive for the visible light wavelength band.

Clause 2. The binocular device of clause 1, further comprising
  a left display and a right display coupled to the support structure and arranged to be viewed by a pair of eyes of a user through a left eyepiece operatively connected to the left display and a right eyepiece operatively connected to the right display, wherein the left display and the right display are configured to present left and right video images, formed with visible light by the left display and the right display, based respectively on the left and right video signals.

Clause 3. The binocular device of any preceding clause, wherein the input optics of at least the camera that is sensitive to radiation in the invisible wavelength band comprises a polarizing filter comprising at least one layer of a polarizing material.

Clause 4. The binocular device of clause 3, wherein the polarizing filter comprises at least two layers of the polarizing material, having a mutually orthogonal polarization direction.

Clause 5. The binocular device of any preceding clause, further comprising a light source coupled to the support structure, capable of generating radiation within at least the invisible wavelength band and the visible light wavelength band, wherein the light source is configured to generate beams of emitted visible light and invisible radiation that are aligned to be substantially identical in geometrical shape and position.

Clause 6. The binocular device of clause 3, further comprising
  a light source coupled to the support structure, capable of generating radiation within at least the invisible wavelength band and the visible light wavelength band, wherein the light source further comprises a polarizing filter configured to polarize the visible light within the visible light wavelength band output by the light source and transmit the radiation in the invisible wavelength band;
  wherein a polarization direction of the polarizing filter of the light source is substantially orthogonal to a polarization direction of the polarizing filter of the input optics.

Clause 7. The binocular device of any preceding clause, wherein the input optics corresponding to the camera that is sensitive to invisible radiation comprises a diaphragm having an aperture, the diaphragm around the aperture being reductive for light in the visible light wavelength band, while the diaphragm is transmissive for the light in the invisible wavelength band.

Clause 8. The binocular device of clause 7, wherein the input optics comprises a lens with autofocus, wherein the autofocus is configured to bring into focus the radiation in the invisible wavelength band.

Clause 9. The binocular device of clause 7, wherein the input optics of the camera that is sensitive to radiation in the invisible wavelength band further comprises a filter that is reductive for the light in the visible light wavelength band in addition to the diaphragm.

Clause 10. The binocular device of any preceding clause, wherein the input optics of the camera that is sensitive to radiation of the invisible wavelength band comprises a filter comprising iodine for selectively reducing the radiation in the visible light wavelength band.

Clause 11. The binocular device of any preceding clause, further comprising a processing unit configured to:
receive a signal representing a left image from the left camera and a right image from the right camera, the left image and the right image being captured substantially simultaneously by the left camera and the right camera, respectively;
 compare the left image to the right image; and
 detect a specular reflection based on a result of the comparison.

Clause 12. The binocular device of any preceding clause, further comprising
 a light source coupled to the support structure, for generating at least radiation in the invisible wavelength band and visible light, wherein the light source is configured to intermittently emit the invisible light while keeping the visible light intensity substantially constant, wherein the camera is configured to capture at least one image with the emitted invisible light and at least one image without the emitted invisible light.

Clause 13. The binocular device of clause 12, further comprising a processing unit configured to calculate an enhanced image of radiation in the invisible wavelength band based on the captured image with the emitted invisible light and the captured image without the emitted invisible light.

Clause 14. The binocular device of any preceding clause, wherein each of the left camera and the right camera is sensitive to radiation in the invisible wavelength band and radiation in the visible light wavelength band, each of the left input optics and the right input optics being transmissive for the invisible wavelength band and reductive for the visible light wavelength band.

Clause 15. The binocular device of any preceding clause, wherein the image sensor of the camera that is sensitive to the radiation in the invisible wavelength band comprises a sensor die that is sensitive to both the invisible wavelength band of radiation and the visible wavelength band of radiation, wherein the sensor die is configured to output the video signal corresponding to both the radiation in the invisible wavelength band and the radiation in the visible wavelength band.

Clause 16. The binocular device of any preceding clause, wherein the invisible wavelength band of radiation is a near-infrared wavelength band of radiation.

Clause 17. A method of visualizing visible and invisible radiation, comprising
 receiving radiation, about a same field of view along respective left and right input optical axes, by left and a right input optics coupled to a support structure, and transmitting the light onto a left image sensor of a left camera and a right image sensor of a right camera, respectively, the left camera and the right camera being coupled to the support structure, wherein at least one of the cameras is sensitive to both radiation in an invisible wavelength band of radiation and radiation in a visible light wavelength band of radiation, wherein the input optics of the camera that is sensitive to the invisible wavelength band of radiation is transmissive for the invisible wavelength band of radiation and reductive for the visible light wavelength band of radiation; and
 creating left and right video signals from the detected radiation received by the left camera and the right camera, respectively.

Clause 18. The method of clause 17, further comprising presenting, by a left display and a right display coupled to the support structure and to be viewed by a pair of eyes of a user through a left eyepiece operatively connected to the left display and a right eyepiece operatively connected to the right display, left and right video images formed with visible light based respectively on the left and right video signals.

The invention claimed is:

1. A binocular device for visualizing optical radiation, comprising
 a support structure;
 a left camera and a right camera coupled to the support structure, the left camera comprising left input optics and a left image sensor, the right camera comprising right input optics and a right image sensor, the left image sensor and the right image sensor being configured to create left and right video signals from detected optical radiation received from the corresponding left and right input optics about a same field of view along respective left and right input optical axes;
 the device further comprising a processing unit configured to:
 receive a signal representing a left image from the left camera and a right image from the right camera, the left image and the right image being captured substantially simultaneously by the left camera and the right camera, respectively;
 compare the left image to the right image; and
 detect a specular reflection based on a result of the comparison.

2. The binocular device of claim 1, further comprising a left display and a right display coupled to the support structure and arranged to be viewed by a pair of eyes of a user through a left eyepiece operatively connected to the left display and a right eyepiece operatively connected to the right display, wherein the left display and the right display are configured to present left and right video images, formed with visible light by the left display and the right display, based respectively on the left and right video signals.

3. The binocular device of claim 1, wherein at least one of the cameras is sensitive to both radiation in an invisible wavelength band of radiation and radiation in a visible light wavelength band of radiation, wherein the corresponding left or right input optics of said at least one of the cameras is transmissive for the invisible wavelength band and reductive for the visible light wavelength band.

4. The binocular device of claim 3, wherein the input optics of at least the camera that is sensitive to radiation in the invisible wavelength band comprises a polarizing filter comprising at least one layer of a polarizing material.

5. The binocular device of claim 4, wherein the polarizing filter comprises at least two layers of the polarizing material, the two layers of the polarizing material having a mutually orthogonal polarization direction.

6. The binocular device of claim 3, further comprising a light source coupled to the support structure, capable of generating radiation within at least the invisible wavelength band and the visible light wavelength band, wherein the light source is configured to generate beams of emitted visible light and invisible radiation that are aligned to be substantially identical in geometrical shape and position.

7. The binocular device of claim 4, further comprising
a light source coupled to the support structure, capable of generating radiation within at least the invisible wavelength band and the visible light wavelength band, wherein the light source further comprises a polarizing filter configured to polarize the visible light within the visible light wavelength band output by the light source and transmit the radiation in the invisible wavelength band;
wherein a polarization direction of the polarizing filter of the light source is substantially orthogonal to a polarization direction of the polarizing filter of the input optics.

8. The binocular device of claim 3, wherein the input optics corresponding to the camera that is sensitive to invisible radiation comprises a diaphragm having an aperture, the diaphragm around the aperture being reductive for light in the visible light wavelength band, while the diaphragm is transmissive for the light in the invisible wavelength band.

9. The binocular device of claim 8, wherein the input optics comprises a lens with autofocus, wherein the autofocus is configured to bring into focus the radiation in the invisible wavelength band.

10. The binocular device of claim 8, wherein the input optics of the camera that is sensitive to radiation in the invisible wavelength band further comprises a filter that is reductive for the light in the visible light wavelength band in addition to the diaphragm.

11. The binocular device of claim 3, wherein the input optics of the camera that is sensitive to radiation of the invisible wavelength band comprises a filter comprising iodine for selectively reducing the radiation in the visible light wavelength band.

12. The binocular device of claim 1, further comprising
a light source coupled to the support structure, for generating at least radiation in the invisible wavelength band and visible light, wherein the light source is configured to intermittently emit the invisible light while keeping the visible light intensity substantially constant, wherein the camera is configured to capture at least one image with the emitted invisible light and at least one image without the emitted invisible light.

13. The binocular device of claim 12, further comprising a processing unit configured to calculate an enhanced image of radiation in the invisible wavelength band based on the captured image with the emitted invisible light and the captured image without the emitted invisible light.

14. The binocular device of claim 1, wherein each of the left camera and the right camera is sensitive to radiation in the invisible wavelength band and radiation in the visible light wavelength band, each of the left input optics and the right input optics being transmissive for the invisible wavelength band and reductive for the visible light wavelength band.

15. The binocular device of claim 1, wherein at least one of the cameras is sensitive to both radiation in an invisible wavelength band of radiation and radiation in a visible light wavelength band of radiation, wherein the corresponding left or right image sensor of the at least one camera comprises a sensor die that is sensitive to both the invisible wavelength band of radiation and the visible wavelength band of radiation, wherein the sensor die is configured to output the video signal corresponding to both the radiation in the invisible wavelength band and the radiation in the visible wavelength band.

16. The binocular device of claim 1, wherein the invisible wavelength band of radiation is a near-infrared wavelength band of radiation.

17. A method of visualizing optic radiation, comprising
receiving radiation, about a same field of view along respective left and right input optical axes, by left and a right input optics coupled to a support structure, and transmitting the light onto a left image sensor of a left camera and a right image sensor of a right camera, respectively, the left camera and the right camera being coupled to the support structure; and
creating left and right video signals from the detected radiation received by the left camera and the right camera, respectively;
receiving, by a processor, a signal representing a left image from the left camera and a right image from the right camera, the left image and the right image being captured substantially simultaneously by the left camera and the right camera, respectively;
comparing, by the processor, the left image to the right image; and
detecting, by the processor, a specular reflection based on a result of the comparison.

18. The method of claim 17, further comprising
presenting, by a left display and a right display coupled to the support structure and to be viewed by a pair of eyes of a user through a left eyepiece operatively connected to the left display and a right eyepiece operatively connected to the right display, left and right video images formed with visible light based respectively on the left and right video signals.

19. A binocular device for visualizing optical radiation, comprising
a support structure;
a left camera and a right camera coupled to the support structure, the left camera comprising left optics and a left image sensor, the right camera comprising right optics and a right image sensor, the left image sensor and the right image sensor being configured to create left and right video signals from detected optical radiation received from the corresponding left and right input optics about a same field of view along respective left and right input optical axes;
a left display and a right display coupled to the support structure and arranged to be viewed by a pair of eyes of a user through a left eyepiece operatively connected to the left display and a right eyepiece operatively connected to the right display, wherein the left display and the right display are configured to present left and right video images, formed with visible light by the left display and the right display, based respectively on the left and right video signals;

wherein the binocular device is configured to, in a particular visualization mode, alternatingly show a left image based on the left video signals on the left display and a right image based on the right video signals on the right display, to allow a user to distinguish a specular reflection.

* * * * *